US011229612B2

(12) United States Patent
Wright et al.

(10) Patent No.: US 11,229,612 B2
(45) Date of Patent: Jan. 25, 2022

(54) PARENTERAL FORMULATIONS

(71) Applicant: GW Research Limited, Cambridge (GB)

(72) Inventors: Stephen Wright, London (GB); Jitinder Wilkhu, Cambridge (GB)

(73) Assignee: GW Research Limited, Cambridge (GB)

(*) Notice: Subject to any disclaimer, the term of this patent is extended or adjusted under 35 U.S.C. 154(b) by 0 days.

(21) Appl. No.: 16/314,583

(22) PCT Filed: Jun. 29, 2017

(86) PCT No.: PCT/GB2017/051913
§ 371 (c)(1),
(2) Date: Dec. 31, 2018

(87) PCT Pub. No.: WO2018/002636
PCT Pub. Date: Jan. 4, 2018

(65) Prior Publication Data
US 2019/0314296 A1 Oct. 17, 2019

(30) Foreign Application Priority Data
Jul. 1, 2016 (EP) .................................... 1611545

(51) Int. Cl.
| A61K 31/05 | (2006.01) |
| A61K 31/352 | (2006.01) |
| A61K 9/00 | (2006.01) |
| A61K 9/08 | (2006.01) |
| A61K 47/10 | (2017.01) |
| A61K 47/18 | (2017.01) |
| A61K 47/22 | (2006.01) |
| A61K 47/26 | (2006.01) |

(52) U.S. Cl.
CPC ............ *A61K 31/05* (2013.01); *A61K 9/0019* (2013.01); *A61K 9/08* (2013.01); *A61K 31/352* (2013.01); *A61K 47/10* (2013.01); *A61K 47/183* (2013.01); *A61K 47/22* (2013.01); *A61K 47/26* (2013.01)

(58) Field of Classification Search
None
See application file for complete search history.

(56) References Cited

U.S. PATENT DOCUMENTS

| 6,403,126 | B1 | 6/2002 | Webster |
| 6,949,582 | B1 | 9/2005 | Wallace |
| 8,293,786 | B2 | 10/2012 | Stinchcomb |
| 8,673,368 | B2 | 3/2014 | Guy et al. |
| 9,017,737 | B2 | 4/2015 | Kikuchi et al. |
| 9,023,322 | B2 | 5/2015 | Van Damme et al. |
| 9,066,920 | B2 | 6/2015 | Whalley et al. |
| 9,095,554 | B2 | 8/2015 | Lewis et al. |
| 9,125,859 | B2 | 9/2015 | Whalley et al. |
| 9,168,278 | B2 | 10/2015 | Guy et al. |
| 9,259,449 | B2 | 2/2016 | Raderman |
| 9,474,726 | B2 | 10/2016 | Guy et al. |
| 9,522,123 | B2 | 12/2016 | Whalley et al. |
| 9,730,911 | B2 | 8/2017 | Verzura et al. |
| 9,949,936 | B2 | 4/2018 | Guy et al. |
| 9,949,937 | B2 | 4/2018 | Guy et al. |
| 9,956,183 | B2 | 5/2018 | Guy et al. |
| 9,956,184 | B2 | 5/2018 | Guy et al. |
| 9,956,185 | B2 | 5/2018 | Guy et al. |
| 9,956,186 | B2 | 5/2018 | Guy et al. |
| 10,092,525 | B2 | 10/2018 | Guy et al. |
| 10,111,840 | B2 | 10/2018 | Guy et al. |
| 10,137,095 | B2 | 11/2018 | Guy et al. |
| 2004/0049059 | A1 | 3/2004 | Mueller |
| 2004/0110828 | A1 | 6/2004 | Chowdhury et al. |
| 2005/0042172 | A1 | 2/2005 | Whittle |
| 2005/0266108 | A1 | 12/2005 | Flockhart et al. |
| 2006/0039959 | A1 | 2/2006 | Wessling |
| 2007/0060638 | A1 | 3/2007 | Olmstead |
| 2007/0060639 | A1 | 3/2007 | Wermeling |

(Continued)

FOREIGN PATENT DOCUMENTS

| CA | 2737447 | 10/2012 |
| CA | 2859934 | 3/2016 |

(Continued)

OTHER PUBLICATIONS

[No Author Listed] "Cannabidiol Therapy for Aicardi Syndrome" Aug. 2014, 4 pages.
[No Author Listed], Cover and Table of Contents, J Pharmacology and Exp Therapeutics, Feb. 2010, 332(2), 4 pages.
Alger, "Not Too Excited? Thank Your Endocannabinoids," Neuron., Aug. 2006, 51(4):393-395.
American Epilepsy Society, Three Studies Shed New Light on the Effectiveness of Cannabis in Epilepsy, Oct. 14, 2014, 2 pages.
Ames et al., "Anticonvulsant effect of cannabidiol," S. Afr Med. J., Jan. 1986, 69(1):14.
Arain et al., "Pregabalin in the Management of Partial Epilepsy," Neuropsychiatr Dis Treat., Aug. 2009, 5:407-413.
Arslan and Tirnaksiz, "Self-emulsifying Drug Delivery Systems," FABAD J Pharm Sci, 2013,38(1):55-64.

(Continued)

*Primary Examiner* — Kyung S Chang
(74) *Attorney, Agent, or Firm* — Cooley LLP

(57) ABSTRACT

The present invention relates to parenteral cannabinoid formulations, and more particularly to cannabinoid containing intravenous (IV) formulations. Preferably the parenteral containing formulation comprises a cannabinoid; an isotonic agent; a surfactant; and one or more stability enhancers. Furthermore the cannabinoid may be selected from one or more of cannabichromene (CBC), cannabichromenic acid (CBCV), cannabidiol (CBD), cannabidiolic acid (CBDA), cannabidivarin (CBDV), cannabigerol (CBG), cannabigerolpropyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCVA).

16 Claims, No Drawings

(56) References Cited

U.S. PATENT DOCUMENTS

| | | |
|---|---|---|
| 2008/0119544 A1 | 5/2008 | Guy et al. |
| 2008/0188461 A1 | 8/2008 | Guan |
| 2009/0035368 A1* | 2/2009 | Moschwitzer ....... A61K 9/1075 424/452 |
| 2009/0264063 A1 | 10/2009 | Tinsley et al. |
| 2009/0306221 A1 | 12/2009 | Guy et al. |
| 2010/0239693 A1 | 9/2010 | Guy et al. |
| 2010/0317729 A1 | 12/2010 | Guy et al. |
| 2011/0028431 A1 | 2/2011 | Zerbe et al. |
| 2011/0038958 A1 | 2/2011 | Kikuchi et al. |
| 2011/0082195 A1 | 4/2011 | Guy et al. |
| 2012/0004251 A1 | 1/2012 | Whalley et al. |
| 2012/0165402 A1 | 6/2012 | Whalley et al. |
| 2012/0183606 A1 | 7/2012 | Bender et al. |
| 2012/0202891 A1 | 8/2012 | Stinchcomb et al. |
| 2012/0231083 A1 | 9/2012 | Carley et al. |
| 2012/0270845 A1 | 10/2012 | Bannister et al. |
| 2013/0209483 A1 | 8/2013 | McAllister |
| 2013/0245110 A1 | 9/2013 | Guy et al. |
| 2013/0296398 A1 | 11/2013 | Whalley et al. |
| 2014/0100269 A1 | 4/2014 | Goskonda et al. |
| 2014/0110828 A1 | 4/2014 | Otremba et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |
| 2014/0343044 A1 | 11/2014 | Ceulemens |
| 2015/0111939 A1 | 4/2015 | Gruening et al. |
| 2015/0181924 A1 | 7/2015 | Llamas |
| 2015/0320698 A1 | 11/2015 | Whalley et al. |
| 2015/0335590 A1 | 11/2015 | Whalley et al. |
| 2015/0342902 A1 | 12/2015 | Vangara et al. |
| 2015/0343071 A1 | 12/2015 | Vangara |
| 2015/0359755 A1 | 12/2015 | Guy et al. |
| 2015/0359756 A1 | 12/2015 | Guy et al. |
| 2016/0051510 A1 | 2/2016 | Allen et al. |
| 2016/0166498 A1 | 6/2016 | Anastassov |
| 2016/0166514 A1 | 6/2016 | Guy et al. |
| 2016/0166515 A1 | 6/2016 | Guy et al. |
| 2016/0220529 A1 | 8/2016 | Guy et al. |
| 2016/0256411 A1 | 9/2016 | Aung-Din |
| 2017/0007551 A1 | 1/2017 | Guy et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0231923 A1 | 8/2017 | Guy et al. |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Whalley et al. |
| 2018/0071210 A1 | 3/2018 | Wilkhu et al. |
| 2018/0228751 A1 | 8/2018 | Stott et al. |
| 2018/0338931 A1 | 11/2018 | Guy et al. |
| 2019/0083418 A1 | 3/2019 | Guy et al. |
| 2019/0167583 A1 | 6/2019 | Shah et al. |
| 2019/0175547 A1 | 6/2019 | Stott et al. |
| 2019/0321307 A1 | 10/2019 | Guy et al. |
| 2019/0365667 A1 | 12/2019 | Wright et al. |
| 2020/0138738 A1 | 5/2020 | Guy et al. |
| 2020/0179303 A1 | 6/2020 | Guy et al. |
| 2020/0206152 A1 | 7/2020 | Stott et al. |
| 2020/0206153 A1 | 7/2020 | Whalley et al. |
| 2020/0237683 A1 | 7/2020 | Whalley et al. |
| 2020/0297656 A1 | 9/2020 | Guy et al. |
| 2020/0352878 A1 | 11/2020 | Guy et al. |
| 2020/0368179 A1 | 11/2020 | Guy et al. |
| 2021/0015789 A1 | 1/2021 | Guy et al. |
| 2021/0052512 A1 | 2/2021 | Guy et al. |
| 2021/0059949 A1 | 3/2021 | Wilkhu et al. |
| 2021/0059960 A1 | 3/2021 | Wilkhu et al. |
| 2021/0059976 A1 | 3/2021 | Wilkhu et al. |
| 2021/0093581 A1 | 4/2021 | Guy et al. |
| 2021/0145765 A1 | 5/2021 | Guy et al. |
| 2021/0169824 A1 | 6/2021 | Guy et al. |
| 2021/0177773 A1 | 6/2021 | Guy et al. |

FOREIGN PATENT DOCUMENTS

| | | |
|---|---|---|
| CN | 101040855 | 9/2007 |
| CN | 103110582 | 5/2013 |
| CN | 104840967 A | 8/2015 |
| DE | 102012-105063 | 12/2013 |
| EP | 2448637 | 5/2012 |
| EP | 2 741 750 A1 | 6/2014 |
| GB | 2384707 | 8/2003 |
| GB | 2434097 | 7/2007 |
| GB | 2434312 | 7/2007 |
| GB | 2450753 | 1/2009 |
| GB | 0911580.9 | 7/2009 |
| GB | 2456183 | 7/2009 |
| GB | 2471523 | 1/2011 |
| GB | 2478595 | 9/2011 |
| GB | 2479153 | 10/2011 |
| GB | 2471565 | 7/2012 |
| GB | 2478072 | 12/2012 |
| GB | 2478074 | 12/2012 |
| GB | 2492487 | 1/2013 |
| GB | 2487712 | 10/2015 |
| GB | 2531282 | 4/2016 |
| GB | 2539472 A | 12/2016 |
| GB | 2438682 | 12/2017 |
| JP | 2010-270110 A | 12/2010 |
| WO | WO 01/28590 A2 | 4/2001 |
| WO | WO 2002/064109 | 8/2002 |
| WO | WO 2003/099302 | 12/2003 |
| WO | WO 2004/016246 | 2/2004 |
| WO | WO 2004/016277 | 2/2004 |
| WO | WO 2006/054057 | 5/2006 |
| WO | WO 2006/133941 | 12/2006 |
| WO | WO 2007/032962 A2 | 3/2007 |
| WO | WO 2007/083098 | 7/2007 |
| WO | WO 2007/138322 | 12/2007 |
| WO | WO 2008/019146 | 2/2008 |
| WO | WO 2008/019146 A2 | 2/2008 |
| WO | WO 2008/024490 A | 2/2008 |
| WO | WO 2008/094181 | 8/2008 |
| WO | WO 2008/129258 | 10/2008 |
| WO | WO 2008/144475 | 11/2008 |
| WO | WO 2008/021394 | 12/2008 |
| WO | WO 2008/146006 | 12/2008 |
| WO | WO 2009/007697 | 1/2009 |
| WO | WO 2009/007698 | 1/2009 |
| WO | WO 2009/020666 | 12/2009 |
| WO | WO 2010/012506 | 2/2010 |
| WO | WO 2011/001169 | 1/2011 |
| WO | WO 2011/121351 | 10/2011 |
| WO | WO 2012/033478 | 3/2012 |
| WO | WO 2012/093255 | 7/2012 |
| WO | WO 2013/024373 A1 | 2/2013 |
| WO | WO 2013/032351 | 3/2013 |
| WO | WO 2014/146699 | 9/2014 |
| WO | WO 2015/142501 | 9/2015 |
| WO | WO 2015/184127 | 12/2015 |
| WO | WO 2015/193667 | 12/2015 |
| WO | WO 2015/193668 | 12/2015 |
| WO | WO 2016/059405 | 4/2016 |
| WO | WO 2016/084075 | 6/2016 |
| WO | WO 2016/118391 | 7/2016 |
| WO | WO 2016/147186 | 9/2016 |
| WO | WO 2016/022936 | 11/2016 |
| WO | WO 2016/199148 | 12/2016 |
| WO | WO 2017/168138 | 10/2017 |
| WO | WO 2018/002636 | 1/2018 |
| WO | WO 2018/002637 | 1/2018 |
| WO | WO 2018/035030 A1 | 2/2018 |
| WO | WO 2018/037203 | 3/2018 |
| WO | WO 2019/082171 A1 | 5/2019 |

(56) References Cited

FOREIGN PATENT DOCUMENTS

| WO | WO 2019/159174 A1 | 8/2019 |
|---|---|---|
| WO | WO 2020/240184 A1 | 12/2020 |

OTHER PUBLICATIONS

Arzimanoglou et al., "All children who experience epileptic falls do not necessarily have Lennox-Gastaut syndrome . . . but many do," Epileptic Discord, 2011, 13:S3-S13.

AU Third Party Observations for Application No. AU2012314129, dated Mar. 19, 2015, 51 pages.

Avoli et al., "Cellular and molecular mechanisms of epilepsy in the human brain," Prog Neurobiol., 2005, 77(3):166-200.

Bakhsm, "Key Attributes of TKDL," Miftaah-al-Khazaain, 1930, 607-608 (with English translation).

Bancaud et al., "Proposal for Revised Clinical and Electroencephalographic Classification of Epileptic Seizures," Epilepsia, Aug. 1981, 22(4):489-501.

Banerjee et al., "Case Report: Aicardi syndrome: A report of five Indian cases," Neurology India, Mar. 2006, 54(1): 91-93.

Barker-Haliski et al., "How Clinical Development Can, and Should. Inform Translational Science," Neuron, Nov. 2014, 84: 582-593.

Benowitz et al., "Metabolic and Psychophysiologic studies of cannabidiol hexobarbital interaction," Clin Pharmacol Ther., 1980, 28(1):115-120.

Bertram, "The Relevance of Kindling for Human Epilepsy," Epilepsia, Apr. 2007, 48(Suppl. 2):65-74.

Bhatt et al., "Indigenous Plants in Traditional Healthcare System in Kedamath Valley of Western Himalaya," Indian J Tradit Knowl., Apr. 2008, 7(2):300-310.

Bhattacharyya et al., "Modulation of mediotemporal and ventrostriatal function in humans by Delta9-tetrahydrocannabinol: a neural basis for the effects of Cannabis sativa on learning and psychosis," Arch Gen Psychiatry., 2009, 66:442-451.

BipolarHealthGroup.org [online], "Charlotte's Web Hemp Remedy," Bipolar Health Group, available on or before Sep. 6, 2017, retrieved on May 21, 2018, URL <http:/bipolarhealthgroup.org/index.php/charlottes-web-hemp-remedy/>, 6 pages.

Booth et al., "Legalization's opening of medical pot research is dream and nightmare," Denver Post, Dec. 14, 2013, retrieved on Feb. 8, 2017, URL <https://www.denverpost.com/2013/12/14/legalizations-opening-of-medical-pot-research-is-dream-and-nightmare/>, 6 pages.

Bostanci et al., "The effects of octanol on penicillin induced epileptiform activity in rats: An in vivo study," Epilepsy Res., Jul. 27, 2006, 71(2-3):188-194.

Braida et al., "Post-ischemic treatment with cannabidiol prevents electroencephalographic flattening, hyper locomotion and neuronal injury in gerbils" Neuroscience Letters., 2003, 346:61-64.

Brust et al., "Marijuana use and the risk of new onset seizures," Trans Am Clin Climatol Assoc., 1992, 103:176-181.

Carlini et al., "Hypnotic and Antiepileptic Effects of Cannabidiol," J Clin Pharmacol., Aug.-Sep. 1981, 21(8-9 Suppl):417S-427S.

Castel-Branco et al., "The Maximal Electroshock Seizure (MES) Model in the Preclinical Assessment of Potential New Antiepileptic Drugs," Methods Find Exp Clin Pharmacol., 2009, 31(2); 101-106.

Charlotte's Web [online], "When to Expect Results from CW Hemp Oil", Mar. 13, 2017, retrieved on May 21, 2018, URL https://www.cwhemp.com/blog/expecting-results-from-hemp, 6 pages.

Charlotte's Web [online], "Whole-Plant Cannabinoids Outperform Single Molecule Compounds," CWHemp.com, Jan. 11, 2017, retrieved on Jun. 16, 2017, URL <https://www.cwhemp.com/blog/whole-plant-cw-hemp-cannabinoids>, 5 pages.

ChildNeurologyFoundation.org [online], "Disorder Directory: Learn from the Experts—LGS (Lennon-Gastaut Syndrome)," Child Neurology Foundation, available on or before Sep. 6, 2005, retrieved on May 21, 2018, URL http://www.childneurologyfoundation.org/disorders/lgs-lennox-gastaut-syndrome, 10 pages.

Chiron and Dulac, "The Pharmacologic Treatment of Dravet Syndrome," Epilepsia, 2011, 52(Suppl. 2): 72-75.

Chiu et al., "The Influence of Cannabidiol and Δ9-Tetrahydrocannabinol on Cobalt Epilepsy in Rats," Epilepsia., 1979, 20:365-375.

Conry et al., "Clobazam in the treatment of Lennox-Gastaut syndrome," Epilepsia, May 2009, 50(5):1158-1166.

Consroe and Sandyk, "Chapter 12: Potential Role of Cannabinoids for Therapy of Neurological Disorders," Marijuana / Cannabinoids: Neurobiology and Neurophysiology, ed. L. Murphy, 1992, 459-524.

Consroe et al., "Anticonvulsant drug antagonism of $\Delta^9$ tetrahydrocannabinol-induced seizures in rabbits," Res Commun Chem Pathol Pharmacol., Jan. 1977, 16(1):1-13.

Consroe et al., "Anticonvulsant Interaction of Cannabidiol and Ethosuximide in Rats," J. Pharm. Pharmac., Aug. 1977, 29(8):500-501.

Consroe et al., "Anticonvulsant Nature of Marihuana Smoking," JAMA, Oct. 1975, 234(3):306-307.

Consroe et al., "Cannabidiol—Antiepileptic Drug Comparisons and Interactions in Experimentally Induced Seizures in Rats," J. Pharm. Exp. Therap., Apr. 1977, 201(1):26-32.

Consroe et al., "Effects of Cannabidiol on Behavioral Seizures Caused by Convulsant Drugs or Current in Mice," Eur J Pharm, Sep. 1982, 83(3-4):293-298.

Consroe et al., "Chapter 2: Therapeutic Potential of Cannabinoids in Neurological Disorders," Cannabinoids as Therapeutic Agents, R. Mechoulam ed., 1986, 21-49.

Cortesi et al., "Potential therapeutical effects of cannabidiol in children with pharmacoresistant epilepsy," Med Hypotheses., 2007, 68(4):920-921.

Cortez and Snead, "Chapter 10: Pharmacologic Models of Generalized Absence Seizures in Rodents," Models of Seizures and Epilepsy, 2006, 111-126.

Crespel, et al., "Chapter 14: Lennox-Gastaut Syndrome," Epileptic Syndromes in Infancy, Childhood, and Adolescence, 2012, 5th Edition, ed. M. Bureau, 189-216.

Cunha et al., "Chronic Administration of Cannabidiol to Healthy Volunteers and Epileptic Patients," Pharmacology, 1980, 21(3):175-185.

Czapinski et al., "Mar. 17, 2008: Randomized 36-month comparative study of valproic acid (VPA), phenytoin (PHT), phenobarbital (PB) and carbamazepine (CBZ) efficacy in patients with newly diagnosed epilepsy with partial complex seizures," J. Neurol. Sci., Sep. 1997, 150(1):S162-S163.

Dasa et al., "Key Attributes of TKDL: Ganja," Brhat Nighantu Ratnakara (Saligramanighantubhusanam), 1997, 6 pages (with English translation).

Davis and Ramsey, "Antiepileptic action of marihuana-active substances," Federation Proceedings., Mar. 1949, 8:284-285.

Davis et al., "A Predominant Role for Inhibition of the Adenylate Cyclase/Protein Kinase A Pathway in ERK Activation by Cannabinoid Receptor 1 in NIE-115 Neuroblastoma Cells," J Biol Chem., Dec. 2003, 278(49): 48973-48980.

De Meijer, "Chapter 5: The Chemical Phenotypes (Chemotypes) of Cannabis," Handbook of Cannabis, ed. Roger G. Pertwee, 2014, 89-110.

De Oliveira, et al., "Anticonvulsant activity of β-caryophyllene against pentylenetetrazol-induced seizures," Epilepsy Behav, Mar. 2016, 56:26-31.

Deshpande et al., "Cannabinoid CBI Receptor Antagonists Cause Status Epilepticus-like Activity in the Hippocampal Neuronal Culture Model of Acquired Epilepsy," Neurosci Lett., Jan. 2007, 411: 11-16.

Devinsky et al., "Cannabidiol: Pharmacology and potential therapeutic role in epilepsy and other neuropsychiatric disorders," Epilepsia, 2014, 55(6):791-802.

Dravet, "The core Dravet syndrome phenotype," Epilepsia, Apr. 2011, 52(Suppl 2): 3-9.

Dreifus et al., "Proposal for Revised Clinical and Electroencephalographic Classification of Epileptic Seizures," Epilepsia, Aug. 1981, 22:489-501.

Dulac and Kaminska, "Use of Lamotrigine in Lennox-Gastaut and Related Epilepsy Syndromes," J. Child Neurolog., Nov. 1997, 12(S1): S23-S29.

(56) References Cited

OTHER PUBLICATIONS

Dulac et al., "Vigabatrin in Childhood Epilepsy," J. Child Neurolog., 1991, 6(S2): S30-S37.
Eadie, "Shortcomings in the current treatment of epilepsy," Expert Rev Neurother., Dec. 2012, 12(12): 1419-1427.
Eggers, "Temporal lobe epilepsy is a disease of faulty neuronal resonators rather than oscillators, and all seizures are provoked, usually by stress," Med Hypotheses, 2007, 69(6): 1284-1289.
ElSohly and Gul, "Chapter 1: Constituents of Cannabis Sativa," Handbook of Cannabis, 2014, ed. Roger G. Pertwee, 3-22.
Engel et al., "Chapter 1: What Should be Modeled?," In Models Seizure Epilepsy., 2006, 14 pages.
Engel, "Report of the ILAE Classification Core Group," Epilepsia, 2006, 47(9):1558-1568.
EPO Annex to the Communication in Opposition for European Appln. No. 10734541.5, dated Jan. 28, 2016, 5 pages.
EPO Auxiliary Requests to the File in European Patent No. EP2448637, dated Nov. 2, 2016, 45 pages.
EPO Communication of a Notice of Opposition in European Appln. No. 10734541.5, dated Dec. 17, 2014, 1 page.
EPO Communication Pursuant to Article 94(3) EPC in European Appln. No. 10734541.5, dated Oct. 23, 2012, 3 pages.
EPO Interlocutory Decision in Opposition in European Appln. No. EP2448637, dated Dec. 15, 2016, 91 pages.
EPO Letter from Opponent Regarding Oral Proceedings in European Patent No. EP2448637, dated Oct. 20, 2016, 6 pages.
EPO Notice of Appeal in European Patent No. EP2448637, dated Feb. 14, 2017, 5 pages.
EPO Notice of Opposition to a European Patent No. EP2448637, Dated Dec. 5, 2014, 20 pages.
EPO Opponent Response to the Preliminary Opinion of the Opposition Division in European Patent No. EP2448637, dated Jun. 23, 2016, 27 pages.
EPO Opponent Response to the Preliminary Opinion of the Opposition Division in European Patent No. EP2448637, dated Sep. 9, 2016, 25 pages.
EPO Opponent Response to the Written Submissions in European Patent No. EP2448637, dated Oct. 12, 2016, 18 pages.
EPO Opponent Response to the Written Submissions in European Patent No. EP2448637, dated Oct. 20, 2016, 3 pages.
EPO Opponent Written Submission in European Patent No. EP2448637, dated Nov. 4, 2016, 3 pages.
EPO Opposition, Expert Statement of Dr. Emma Louise Cheetham in European Appln. No. EP10734541.5, dated Nov. 4, 2016, 1 pages.
EPO Opposition, Expert Statement of Professor Anthony G Marson in European Appln. No. EP10734541.5 , dated Jun. 14, 2016, 9 pages.
EPO Opposition, Expert Statement of Professor Benjamin J. Whalley in European Appln. No. EP10734541.5, dated Sep. 9, 2016, 11 pages.
EPO Opposition, Expert Statement of Vincenzo Di Marzo in European Appln. No. EP10734541.5, dated Sep. 9, 2016, 10 pages.
EPO Opposition, Supplemental Expert Statement of Professor Benjamin J. Whalley, dated Nov. 4, 2016, 9 pages.
EPO Reply of the Patent Proprietor to the Notice(s) of Opposition in European Patent No. 2448637, dated May 28, 2015, 12 pages.
EPO Reply to Examination Report in European Patent Application No. 10734541.5, dated Feb. 15, 2013, 54 pages.
EPO Reply to Opponent's Written Submission in European Patent No. EP2448637, dated Nov. 4, 2016, 13 pages.
EPO Reply to Opponent's Written Submissions in European Patent No. EP2448637, dated Oct. 18, 2016, 5 pages.
EPO Reply to Preliminary Opinion and Opponent's Observations in European Patent No. EP2448637, dated Sep. 9, 2016, 65 pages.
EPO Reply to Proprietor's Statement of Grounds of Appeal in European Patent No. EP2448637, dated Sep. 8, 2017, 5 pages.
EPO Response to the Statement of Grounds of Appeal in European Patent No. 2448637, dated Sep. 5, 2017, 17 pages.
EPO Statement of Grounds of Appeal in European Appln. No. 10734541.5 , dated Apr. 21, 2017, 14 pages.
EPO Statement of Grounds of Appeal in European Appln. No. 10734541.5, dated Apr. 12, 2017, 6 pages.
EPO Statement of Opposition in European Appln. No. EP10734541.5, dated Dec. 5, 2014, 14 pages.
EPO Third Party Observations in European Appln. No. EP10734541.5, dated Apr. 3, 2017, 19 pages.
EPO Third Party Observations in European Appln. No. EPl 1712658.1, dated Nov. 22, 2013, 14 pages.
Fariello, "Parenteral Penicillin in Rats: An Experimental Model of Multifocal Epilepsy," Epilepsia, 1976, 17:217-222.
FDA [online], "Warning Letters and Test Results for Cannabidiol-Related Products," 2015 Warning Letters, retrieved on Nov. 14, 2017, URL <https://www.fda.gov/newsevents/publichealthfocus/ucm484109.htm>, 4 pages.
FDA [online], "Warning Letters and Test Results for Cannabidiol-Related Products," 2016 Warning Letters, retrieved on Nov. 14, 2017, URL <https://www.fda.gov/newsevents/publichealthfocus/ucm484109.htm> , 4 pages.
FDA, Guidance for Industry: Estimating the maximum Safe Starting Dose in Initial Clinical Trials for Therapeutics in Adult Healthy Volunteers, U.S. Dept of Health and Human Services: Food and Drug Administration, Jul. 2005, 30 pages.
Ferdinand et al., "Cannabis—Psychosis Pathway Independent of Other Types of Psychopathology," Schizophrenia Research, 2005, 79:289-295.
Fisher et al., "The impact of epilepsy from the patient's perspective I. Descriptions and subjective perceptions," Epilepsy Research, 2000, 41(1):39-51.
Gabor et al., "Lorazepam Versus Phenobarbital: Candidates for Drug of Choice for Treatment of Status Epilepticus," J Epilepsy, Jan. 1990, 3(1):3-6.
Gallily et al., "Overcoming the Bell-Shaped Dose-Response of Cannabidiol by Using Cannabis Extract Enriched in Cannabidiol," Pharmacology & Pharmacy, Jan. 2015, 6:75-85.
Gardner [online], "Comes Now Epidiolex (FDA Approves IND Studies of CBD)," BeyondTHC.com, Oct. 22, 2013, retrieved on Jan. 31, 2018, URL <http://www.beyondthc.com/comes-now-epidiolex-fda-approves-ind-studies-of-cbd>, 4 pages.
Gastaut., "Clinical and Electroencephalographical Classification of Epileptic Seizures," Epilepsia, 1970, 11:102-113.
GB Combined Search and Examination Report in GB Appln. No. GB1116789.7, dated Jan. 4, 2012, 8 pages.
GB Combined Search and Examination Report in Application No. GB1611544.6, dated Mar. 29, 2017, 8 pages.
GB Combined Search and Examination Report in GB Appln. No. GB1100043.7, dated Mar. 25, 2011, 8 pages.
GB Combined Search and Examination Report in GB Appln. No. GB1121919.3, dated Feb. 29, 2012, 8 pages.
GB Combined Search and Examination Report in GB Appln. No. GB 1410771.8, dated Feb. 27, 2015, 7 pages.
GB Combined Search and Examination Report in GB Appln. No. GB1414813.4, dated Sep. 5, 2014, 8 pages.
GB Combined Search and Examination Report in GB Appln. No. GB1418166.3, dated Jul. 2, 2015, 8 pages.
GB Combined Search and Examination Report in GB Appln. No. GB1418170.5, dated Jul. 2, 2015, 6 pages.
GB Combined Search and Examination Report in GB Appln. No. GB1418171.3, dated Jun. 29, 2015, 8 pages.
GB Combined Search and Examination Report in GB Appln. No. GB1506550.1, dated Feb. 5, 2016, 9 pages.
GB Combined Search and Examination Report in GB Appln. No. GB1514079.1, dated May 4, 2016, 9 pages.
GB Combined Search and Examination Report in GB Appln. No. GB 1605448.8, dated Jan. 12, 2017, 6 pages.
GB Examination Report in GB Appln, No. GB1100043,7, dated Mar. 18, 2014, 2 pages.
Gedde [online], "Clinical Experience with Cannabis in Treatment-Resistant Pediatric Epilepsy," Marijuana for Medical Professionals Conference, Sep. 9-11, 2014, URL <http://www.theroc.us/images/gedde_presentation.pdf, Sep. 9-11, 2014>, 45 pages.

(56) References Cited

OTHER PUBLICATIONS

Gedde et al., "3.330: Whole Cannabis Extract of High Concentration Cannabidiol May Calm Seizures in Highly Refractory Pediatric Epilepsies," American Epilepsy Society, Dec. 2013, 449-450.
Geffrey et al., "Cannabidiol (CBD) Treatment for Refractory Epilepsy," American Epilepsy Society, Annual Meeting Abstract 2.427, 2014, retrieved on Feb. 10, 2017, URL <https://www.aesnet.org/meetings_events/annual_meeting_abstracts/view/1868979>, 2 pages.
Green [online], "CBD: An Unconventional Therapy," Nugs.com, Mar. 24, 2014, URL <http://nugs.com/article/cbd-an-unconventional-therapy.html>, 5 pages.
Gresham et al., "Treating Lennox-Gastaut syndrome in epileptic pediatric patients with third generation rufinamide," Neuropsychiatr Dis Treat, Oct. 5, 2010, 6:639-645.
Gross et al., "Marijuana use and Epilepsy: Prevalence in Patients of a Tertiary Care Epilepsy Center," Neurology, Jun. 8, 2004, 62(11):2095-2097.
Guerrini et al., "Lamotrigine and Seizure Aggravation in Severe Myoclonic Epilepsy," Epilepsia, 1998, 39(5):508-512.
Guimaraes et al., "Antianxiety effect of cannabidiol in the elevated plus-maze," Psychopharmacology, 1990, 100: 558-559.
GWPharm [online], "GW Pharmaceuticals Announces Epidiolex(R) Receives Fast Track Designation from FDA for the Treatment of Dravet Syndrome," GW Pharmaceuticals Press Release, Jun. 6, 2014, retrieved on Mar. 1, 2017, URL <https://www.gwpharm.com/about-us/news/gw-pharmaceuticals-announces-epidiolex%C2%AE-receives-fast-track-designation-fda-treatment>, 2 pages.
GWPharm [online], "GW Pharmaceuticals Announces Physician Reports of Epidiolex(R) Treatment Effect in Children and Young Adults with Treatment-resistant epilepsy from Physician-Led Expanded Access Treatment Program," GW Pharmaceuticals Press Release, Jun. 17, 2014, retrieved on May 1, 2017, URL <https://www.gwpharm.com/about-us/news/gw-pharmaceuticals-announces-physician-reports-epidiolex%C2%AE-treatment-effect-children>, 8 pages.
GWPharm [online], "GW Pharmaceuticals Announces Preliminary Results of Phase 2a Study for its Pipeline Compound GWP42006," GW Pharmaceuticals Press Release, Feb. 21, 2018, retrieved on Jun. 29, 2018, URL <https://www.gwpharm.com/about-us/news/gw-pharmaceuticals-announces-preliminary-results-phase-2a-study-its-pipeline-compound>, 5 pages.
GWPharm [online], "GW Pharmaceuticals Provides Update on Orphan Program in Childhood Epilepsy for Epidiolex®," GW Pharmaceuticals Press Release, Nov. 15, 2013, retrieved on Jun. 20, 2018, URL <https://www.gwpharm.com/about-us/news/gw-pharmaceuticals-provides-update-orphan-program-childhood-epilepsy-epidiolex%C2%AE>, 5 pages.
GWPharm [online], "GW Pharmaceuticals Receives Orphan Drug Designation by FDA for Epidiolex® in the Treatment of Lennox-Gastaut Syndrome," GW Pharmaceuticals Press Release, Feb. 28, 2014, retrieved on Feb. 10, 2017, URL <https://www.gwpharm.com/about-us/news/gw-pharmaceuticals-receives-orphan-drug-designation-fda-epidiolex%C2%AE-treatment-lennox>, 4 pages.
GWPharm [online], "Orphan Drug Designation Granted for Epidiolex in Dravet syndrome by the FDA—Seven Expanded Access INDs granted by FDA to US physicians to treat with Epidiolex 125 children suffering from intractable epilepsy syndromes," GW Pharmaceuticals Press Release, Nov. 15, 2013, retrieved on Feb. 10, 2017, URL <https://www.gwpharm.com/about-us/news/gw-pharmaceuticals-provides-update-orphan-program-childhood-epilepsy-epidiolex%C2%AE>, 5 pages.
Heinemann et al., "Chapter 4: An Overview of In Vitro Seizure Models in Acute and Organotypic Slices," Models of Seizures and Epilepsy, 2006 35-44.
Hill et al., "$\Delta^9$-Tetrahydrocannabivarin suppresses in vitro epileptiform and in vivo seizure activity in adult rats," Epilepsia, Aug. 2010, 51(8):1522-1532.
Hill, "Cannabidivarin-rich cannabis extracts are anticonvulsant in mouse and rat via a CB1 receptor-independent mechanism," British Journal of Pharmacology, Oct. 2013, 170(3): 679-692.
Holmes et al. "Choosing the Correct AED: From Animal Studies to the Clinic," Pediatr Neurol, Mar. 2008, 38(3): 151-162.
Iannotti et al., "Nonpsychotropic plant cannabinoids, cannabidivarin (CBDV) and cannabidiol (CBD), activate and desensitize transient receptor potential vanilloid 1 (TRPV1) channels in vitro: Potential for the treatment of neuronal hyperexcitability," ACS Chem. Neurosci., Jul. 16, 2014, 5:1131-1141.
ICE Epilepsy Alliance, The Dravet Syndrome Spectrum, Nov. 2008, 2 pages.
*Insys Development Company, Inc. v. GW Pharma Limited and Otsuka Pharmaceutical Co., Ltd.*, Decision in IPR2017-00503, U.S. Pat. No. 9,066,920, dated Jul. 7, 2017, 26 pages.
*Insys Development Company, Inc. v. GW Pharma Limited and Otsuka Pharmaceutical Co., Ltd.*, Declaration by Mark Polyakov, IPR2017-00503, U.S. Pat. No. 9,066,920, dated May 29, 2018, 1 page.
*Insys Development Company, Inc. v. GW Pharma Limited and Otsuka Pharmaceutical Co., Ltd.*, Declaration of Professor Anthony G. Marson in IPR2017-00503, U.S. Pat. No. 9,066,920, dated Dec. 13, 2016, 28 pages.
*Insys Development Company, Inc. v. GW Pharma Limited and Otsuka Pharmaceutical Co., Ltd.*, Declaration of Professor H. Steve White in IPR2017-00503, U.S. Pat. No. 9,066,920, dated Oct. 24, 2017, 69 pages.
*Insys Development Company, Inc. v. GW Pharma Limited and Otsuka Pharmaceutical Co., Ltd.*, Declaration of Professor Leslie Benet in IPR2017-00503, U.S. Pat. No. 9,066,920, dated Nov. 22, 2016, 18 pages.
*Insys Development Company, Inc. v. GW Pharma Limited and Otsuka Pharmaceutical Co., Ltd.*, Deposition of H. Steve White, dated Dec. 13, 2016, 50 pages.
*Insys Development Company, Inc. v. GW Pharma Limited and Otsuka Pharmaceutical Co., Ltd.*, Final Written Decision in IPR2017-00503, U.S. Pat. No. 9,066,920, dated Jan. 3, 2019, 40 pages.
*Insys Development Company, Inc. v. GW Pharma Limited and Otsuka Pharmaceutical Co., Ltd.*, Patent Owners' Preliminary Response in IPR2017-00503, U.S. Pat. No. 9,066,920, dated Apr. 11, 2017, 45 pages.
*Insys Development Company, Inc. v. GW Pharma Limited and Otsuka Pharmaceutical Co., Ltd.*, Petition for Inter Partes Review, IPR2017-00503, U.S. Pat. No. 9,066,920, dated Dec. 16, 2016, 78 pages.
*Insys Development Company, Inc. v. GW Pharma Limited and Otsuka Pharmaceutical Co., Ltd.*, Petitioner's Brief Regarding Ground III of the IPR, IPR2017-00503, U.S. Pat. No. 9,066,920, dated May 29, 2018, 45 pages.
*Insys Development Company, Inc. v. GW Pharma Limited and Otsuka Pharmaceutical Co., Ltd.*, Petitioner's Reply to Patent Owner's Response, IPR2017-00503, U.S. Pat. No. 9,066,920, dated Jun. 19, 2018, 6 pages.
*Insys Development Company, Inc. v. GW Pharma Limited and Otsuka Pharmaceutical Co., Ltd.*, Petitioner's Reply to Response in IPR2017-00503, U.S. Pat. No. 9,066,920, dated Jan. 19, 2018, 36 pages.
IUPHAR/BPS Guide to Pharmacology [online], "Entry for Δ9-tetrahydrocannabidiol," available on or before Mar. 29, 2016, retrieved on Jun. 20, 2018, URL <http://www.guidetopharmacology.org/GRAC/LigandDisplayForward?tab=biology&ligandId=242>, 2 pages.
Iuvone et al., "Neuroprotective Effect of Cannabidiol, a Non-psychoactive Component From Cannabis Sativa, on β-amyloid-induced toxicity in PC12 Cells," J Neurochem, Apr. 2004, 89(1):134-41.
Izzo et al., "Non-psychotropic plant cannabinoids: new therapeutic opportunities from an ancient herb," Trends in Pharmacological Sciences, 2009, 30(10):515-527.
Jacobson and Porter, "Survey of Current Cannabidiol Use in Pediatric Treatment-Resistant Epilepsy", Apr. 2013, URL <https://www.thcint.com/uploads/1/9/3/7/19371199/cannabidiol_use_in_pediatric_epilepsy.pdf>, 1 page.
Jeavons et al., "Sodium Calproate in Treatment of Epilepsy," Br Med J., Jun. 15, 1974, 2(5919):584-586.

(56) References Cited

OTHER PUBLICATIONS

Jones et al. [online], Info & Metrics / Article Information, "Cannabidiol Displays Antiepileptiform and Antiseizure Properties in Vitro and in Vivo," J Pharmacol Exp Then, Feb. 2010, 332(2):569-577, retrieved on Jun. 25, 2018, URL: http://jpet.aspetjournals.org/content/332/2/569/tab-article-info, 9 pages.
Jones et al., "Cannabidiol Displays Antiepileptiform and Antiseizure Properties in Vitro and in Vivo," J Pharmacol Exp Ther., Feb. 2010, 332(2):559-577.
Joy et al., "Marijuana and Medicine: Assessing the Science Base", Institute of Medicine, National Academy Press, 1999, 170 pages.
Kahan et al., "Risk of Selection Bias in Randomized Trials," Trials, Sep. 2015, 16:405, 7 pages.
Kaplan, "F.D.A. Panel Recommends Approval of Cannabis-Based Drug for Epilepsy," NY Times, Apr. 19, 2018, retrieved on Jun. 20, 2018, URL <https://www.nytimes.com/2018/04/19/health/epidiolex-fda-cannabis-marajuana.html>, 3 pages.
Karler et al., "The Cannabinoids as Potential Antiepileptics," J Clin Pharmacol., Aug.-Sep. 1981, 21:437S-448S.
Kelley et al., "Doose syndrome (myoclonic-astatic epilepsy): 40 years of progress," Developmental Medicine & Child Neurology, Aug. 2010, 52: 988-993.
Khan et al., "Key Attributes of TKDL: Laooq-e-Qinnab/Barai Zeequn-Nafs," Khazaain-al-Advia, 1911, 2 pages (with English translation).
Khan et al., "Key Attributes of TKDL: Nuskha-e-Qutoor," Muheet-e-Azam, 1887, 2 pages (with English translation).
Khan et al., "Key Attributes of TKDL: Sufoof-e-qinnab Barae Waja," Khazaain-al-Adiva, 1911, 5 pages (with English translation).
Khan et al., "Key Attributes of TKDL: Usaara-e-Qinnab Barai Qoolanj," Khazaain-al-Advia, 1911, 6 pages (with English translation).
Khan et al., "Key Attributes of TKDL: Zimad-e-qinnab," Khazaain-al-Adiva, 1911, 5 pages (with English translation).
Klitgaard et al., "Electrophysiological, neurochemical and regional effects of levetiracetam in the rat pilocarpine model of temporal lobe epilepsy," Seizure, Mar. 2003, 12(2):92-100.
Klitgaard et al., "Evidence for a unique profile of levetiracetam in rodent models of seizures and epilepsy," European J Pharm, Jul. 1998, 353(2):491-206.
Kramer et al., "Febrile infection-related epilepsy syndrome (FIRES): pathogenesis, treatment, and outcome: a multicenter study on 77 children," Epilepsia, Nov. 2011, 52(11):1956-1965.
Kwan et al., "Definition of drag resistant epilepsy: consensus proposal by the ad hoc Task Force of the ILAE Commission on Therapeutic Strategies," Epilepsia, Jun. 2010, 51(6):1069-1077.
LeafScience.com [online], "What are the Highest CBD Strains?" Oct. 15, 2014, retrieved on Feb. 16, 2017, URL <www.leafscience.com/2014/10/15/highest-cbd-strains/>, 2 pages.
Leo et al., "Cannabidiol and epilepsy: Rationale and therapeutic potential," Pharamacological Research, Mar. 2016, 107: 85-92.
Lewis, "Mystery Mechanisms," TheScientist.com, Jul. 29, 2016, retrieved on Nov. 8, 2017, URL <https://www.the-scientist.com/?articles.view/articleNo/46688/title/Mystery-Mechanisms/>, 2 pages.
Lieu et al., "Assessment of self-selection bias in a pediatric unilateral hearing loss study," Otolaryngol Head Neck Surg, Mar. 2010, 142(3): 427-433.
Lindamood and Colasanti, "Effects of $\Delta^9$-Tetrahydrocannabinol and Cannabidiol on Sodium-Dependent High Affinity Choline Uptake in the Rat Hippocampus1," J Pharmacology Experimental Therapeutics, 1980, 213(2):216-221.
Long et al., "The Pharmacological actions of cannabidiol," Drugs of the Future, Jul. 2005, 30(7):747-753.
Löscher and Schmidt, "Modern antiepileptic drug development has failed to deliver: ways out of the current dilemma." Epilepsia, Apr. 2011, 52(4):657-78.
Lowenstein "Chapter 363: Seizures and Epilepsy," Diseases of the Central Nervous System, 2008, 2498-2512.
Luttjohann et al., "A Revised Racine's scale for PTZ-induced seizures in rats," Physiology & Behavior, 2009, 98:579-586.

Lutz, "On-demand activation of the endocannabinoid system in the control of neuronal excitability and epileptiform seizures," Biochemical Pharmacology, Nov. 2004, 68(9):1691-1698.
Maa et al., "The Case for Medical Marijuana in Epilepsy," Epilepsia, Jun. 2014, 55(6):783-786.
Mackie, "Cannabinoid Receptors as Therapeutic Targets," Annu Rev Pharmacol Toxicol, 2006, 46:101-122.
Majoosi et al., "Key Attributes of TKDL: Saoot Baraae Sara," Kaamil-al-Sena'ah, Central Council for Research in Unani Medicine, 2005, 2 pages (with English translation).
Malfait et al., "The nonpsychoactive cannabis constituent cannabidiol is an oral anti-arthritic therapeutic in murine collagen-induced arthritis," PNAS, Aug. 15, 2000, 97(17):9561-9566.
Manni et al., "Obstructive Sleep Apnea in a Clinical Series of Adult Epilepsy Patients: Frequency and Features of the Comorbidity," Epilepsia, Jun. 2003, 44(6): 836-840.
Manno, "Status Epilepticus: Current Treatment Strategies," The Neurohospitalist, Jan. 2011, 1(1):23-31.
Mares et al., "Chapter 12: Electrical Stimulation-Induced Models of Seizures," Model of Seizures and Epilepsy, Asia Pitkänen, Philip A. Schwartzkroin & Solomon L. Moshé, eds., 2004, 153-159.
Martin et al., "Structure-Anticonvulsant Activity Relationships of Cannabidiol Analogs," National Institute on Drug Abuse, Research Monograph Series, 1987, 79:48-58.
Mattson et al., "Comparison of carbamazepine, phenobarbital, phenytoin, and primidone in partial and secondarily generalized tonic-clonic seizures," N Engl J Med, Jul. 18, 1985, 313(3):145-151.
Mattson et al., "Prognosis for total control of complex partial and secondary generalized tonic clonic seizures," Neurology, 1996, 47:68-76.
McCormick et al., "On the Cellular Network Bases of Epileptic Seizures," Annu Rev Physiol, 2001, 63:815-846.
McNamara, "Chapter 19: Pharmacotherapy of the Epilepsies,", Goodman & Gilman's The Pharmacological Basis of Therapeutics 11th ed., McGraw-Hill Companies, 2006, 501-525.
Mechoulam et al., "Cannabidiol: An Overview of Some Pharmacological Aspects," J Clin Pharmacol, 2002, 42:11S-19S.
Mechoulam et al., "Toward drugs derived from cannabis," Naturwissenschaften, Apr. 1978, 65(4):174-179.
Medicos [online], "Convulsive Disorders and Their Interference with Driving," Medicos, 2014, retrieved Feb. 10, 2017, URL <https://www.medicosporlaseguridadvial.com/en/clinical-subjects/neurologic-diseases/convulsive-disorders-and-their-interference-with-driving/>, 3 pages.
Merlis, "Proposal for an International Classification of the Epilepsies," Epilepsia, 1970, 11:114-119.
Miller et al., "Mapping genetic modifiers of survival in a mouse model of Dravet syndrome," Genes, Brain and Behavior, 2014, 13:163-172.
Moral et al., "Pipeline on the Move," Drugs of the Future, Jan. 2014, 39(1): 49-56.
Morard et al., "Conversion to Sirolimus-Based Immunosuppression in Maintenance Liver Transplantation Patients," Liver Transplantation, 2007, 13:658-664.
MyVirtualMedicalCentre [online], "Aicardi syndrome," mvmc.com, Feb. 2004, retrieved on Jan. 25, 2019, https://www.myvmc.com/diseases/aicardi-syndrome/, 6 pages.
Neto et al., "The role of polar phytocomplexes on anticonvulsant effects of leaf extracts of Lippia Alba (Mill.) N.E. Brown chemotypes," J. Pharm Pharmacol, 2009, 61(7):933-939.
Ng et al., "Illicit Drug Use and the Risk of New-Onset Seizures," Am J Epidemiol, 1990, 132(1):47-57.
Oakley et al., "Dravet Syndrome Insights into pathophysiology and therapy from a mouse model of Dravet syndrome," Epilepsia, Apr. 2011, 52(Suppl. 2): 59-61.
Obay et al., "Antiepileptic effects of ghrelin on pentylenetetrazole-induced seizures in rats," Peptides, Jun. 2007, 28(6):1214-1219.
PCT International Preliminary Report on Patentability in International Appln. No. PCT/GB2010/051066, dated Jun. 9, 2011, 6 pages.
PCT International Preliminary Report on Patentability in International Appln. No. PCT/GB2012/052284, dated Dec. 12, 2013, 12 pages.

(56) References Cited

OTHER PUBLICATIONS

PCT International Preliminary Report on Patentability in International Appln. No. PCT/GB2015/051775, dated Aug. 10, 2016, 9 pages.
PCT International Preliminary Report on Patentability in International Appln. No. PCT/GB2015/053030, dated Apr. 18, 2017, 6 pages.
PCT International Preliminary Report on Patentability in International Appln. No. PCT/GB2016/051792, dated Sep. 1, 2017, 14 pages.
PCT International Preliminary Report on Patentability in International Appln. No. PCT/US2017/050868, dated Oct. 11, 2018, 7 pages.
PCT International Search Report and Written Opinion in International Appln. No. PCT/GB2010/051066 dated Dec. 13, 2010, 8 pages.
PCT International Search Report and Written Opinion in International Appln. No. PCT/GB2011/050649, dated May 30, 2011, 15 pages.
PCT International Search Report and Written Opinion in International Appln. No. PCT/GB2012/052284, dated Nov. 16, 2012, 11 pages.
PCT International Search Report and Written Opinion in International Appln. No. PCT/GB2015/051775, dated Aug. 26, 2015, 11 pages.
PCT International Search Report and Written Opinion in International Appln. No. PCT/GB2015/051776, dated Aug. 25, 2015, 11 pages.
PCT International Search Report and Written Opinion in International Appln. No. PCT/GB2016/052340, dated Oct. 25, 2016, 12 pages.
PCT International Search Report and Written Opinion in International Appln. No. PCT/US2017/050868, dated Aug. 6, 2017, 14 pages.
PCT International Search Report and Written Opinion in International Appln. PCT/GB2017/051943, dated Sep. 12, 2017, 10 pages.
PCT International Search Report in International Appln. No. PCT/GB2012/050002, dated Feb. 24, 2012, 3 pages.
PCT Interntional Search Report and Written Opinion in International Appln. No. PCT/GB2017/051913, dated Sep. 15, 2017, 9 pages.
PCT Interntional Search Report and Written Opinion in International Appln. No. PCT/GB2017/051914, dated Sep. 12, 2017, 10 pages.
Pelliccia et al. [online], "Treatment with CBD in oily solution of drag-resistant paediatric epilepsies," 2005 Congress on Cannabis and the Cannabinoids, Leiden, The Netherlands: International Association for Cannabis as Medicine, 2005, 14, retrieved on Jun. 30, 2015, URL <http://www.cannabis-med.org/studies/ww_en_db_study_show.php?s_id=173&&search_pattern=EPILEPSY>, 2 pages, Abstract only.
Pereira et al., "Study pharmacologic of the GABAergic and glutamatergic drags on seizures and status epilepticus induced by pilocarpine in adult Wistar rats," Neurosci Lett, Jun. 2007, 419(3):253-257.
Pertwee, "Cannabinoid receptor ligands: clinical and neuropharmacological considerations, relevant to future drag discovery and development," Expert Opin Investig Drags, Jul. 2000, 9(7): 1553-1571.
Pertwee, "Chapter 3: The Pharmacology and Therapeutic Potential of Cannabidiol," Cannabinoids, Ed Vincenzo Di Marzo ed., 2004, 32-83.
Pertwee, "The diverse CB1 and CB2 receptor pharmacology of three plant cannabinoids: Δ9-tetrahydrocannabinol, cannabidiol and Δ9-tetrahydrocannabivarin," Br. J. Pharmacol, 2008, 153(2):199-215.
Petrocellis et al., "Effects of cannabinoids and cannabinoid-enriched Cannabis extracts on TRP channels and endocannabinoid metabolic enzymes," British Journal of Pharmacology, 2011, 163:1479-1494.
Pohl et al., "Effects of flunarizine on Metrazol-induced seizures in developing rats," Epilepsy Res, 1987, 1:302-305.
Poortman-van der Meer, "A contribution to the improvement of accuracy in the quantitation of THC," Forensic Science International, Apr. 1999, 101(1): 1-8.
Porter et al., "Randomized, multicenter, dose-ranging trial of retigabine for partial-onset seizures," Neurology, Apr. 2007, 68(15): 1197-1204.
Porter et al., "Report of a Parent Survey of Cannabidiol-enriched Cannabis use in Pediatric Treatment-resistant Epilepsy," Epilepsy Behavior, Dec. 2013, 29(3): 574-577.
Potter, "Chapter 4: Cannabis Horticulture," Handbook of Cannabis, ed. Roger G. Pertwee, 2014, 65-88.
Pouton, "Lipid formulations for oral administration of drugs: non-emulsifying, self-emulsifying and 'self-microemulsifying' drag delivery systems," Eur. J Pharm Sci, Oct. 2000, 11(Supp. 2): S93-S98.
Press et al., "Parental reporting of response to oral cannabis extracts for treatment of refractory epilepsy," Epilepsy Behav, Apr. 2015, 45:49-52.
Pruitt et al., "Ethanol in Liquid Preparations Intended for Children," Padiatrics, Mar. 1984: 73(3):405-407.
Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.
Ramantani et al., "Epilepsy in Aicardi-Goutieres syndrome," Official J Eur Paediatric Neurology Society, 2014, 18: 30-37.
Rauca et al., "The role of superoxide dismutase and a-tocopherol in the development of seizures and kindling induced by pentylenetetrazol-influence of the radical scavenger a-phenyl-N-tert-butyl nitrone," Brain Research, May 29, 2004, 1009(1-2):203-212.
Resstel et al., "5-HT$_{1A}$ receptors are involved in the cannabidiol-induced attenuation of behavioural and cardiovascular responses to acute restraint stress in rats," Br J Pharmacol, Jan. 2009, 156(1):181-188.
Rosenberg et al., "Cannabinoids and Epilepsy," Neurotherapeutics, Oct. 2015, 12(4): 747-768.
Rosenkrantz et al., "Oral and Parenteral Formulations of Marijuana Constituents," J Pharm Sci, Jul. 1972, 61(7)1106-1112.
Rubio et al., "In Vivo Experimental Models of Epilepsy," Central Nervous System Agents in Medicinal Chemistry, 2010, 10:298-309.
Russo, "Taming THC: potential cannabis synergy and phytocannabinoid-terpenoid entourage effects," British J. of Pharm, 2011, 163:1344-1364.
Sadanandasarma et al., "Key Attributes of TKDL: Suddha Bhanga Visista Gunah Aur Matra," Rasatarangini 11th Ed., 1979:720-723 (with English translation).
SalutarisDrops.com [online], "Cannabidiol for Aicardi Syndrome," Salutaris, available on or before Oct. 2014, retrieved on Feb. 10, 2017, URL <http://web.archive.org/web/20141012220050/http://salutarisdrops.com/cannabidiol-aicardi-syndrome/>, 3 pages.
Sander, "The epidemiology of epilepsy revisited," Curr Opin Neurol, Apr. 2003, 16(2):165-170.
Sastri et al., "Key Attributes of TKDL: Vijaya Kalpah (Apasmaranasaka)," Anandakandam 1st ed., 1952:241, 5 pages (with English translation).
Scuderi et al., "Cannabidiol in Medicine: A Review of its Therapeutic Potential in CNS Disorders," Phytother Res, May 2009, 23(5):597-602.
Shukla [online], "New Automated Purification Strategies for Scale-Up," PCISyntesis.com, posted Dec. 25, 2017, https://www.pcisynthesis.com/new-automated-purification-strategies-for-scale-up/, 5 pages.
Silva et al., "Clobazam as Add-on Therapy in Children with Epileptic Encephalopathy," Can J Neurol Sci, 2006 33: 209-213.
Sperling et al., "Carisbamate as adjunctive treatment of partial onset seizures in adults in two randomized, placebo-controlled trials," Epilepsia, Mar. 2010, 51(3):333-343.
Stafstrom et al., "Models of Pediatric Epilepsies: Strategies and Opportunities," Epilepsia, 2006, 47(8): 1407-1414.
Stephenson, "In Memoriam: Professor Jean Aicardi (1926-2015)," Pediatric Neurology, Jan. 2016, 54: 3-4.
Stott et al., "Cannabinoids for the pharmaceutical industry," Euphytica, 2004, 140:83-93.

(56) References Cited

OTHER PUBLICATIONS

Strickley, "Solubilizing Excipients in Oral and Injectable Formulations," Table VIII, Pharmaceutical Research, Feb. 2004, 21(2): 201-230.

Swann., "The Effects of Seizures on the Connectivity and Circuitry of the Developing Brain," MRDD, 2004, 10(2):96-100.

Thomas et al., "Evidence that the Plant Cannabinoid Δ9-Tetrahydrocannabivarin is a Cannabinoid CB1 and CB2 Receptor antagonist," Br J Pharmacol, Dec. 2005, 146(7):917-926.

Thumma et al., "Influence of plasticizers on the stability and release of a prodrug of Δ9-tetrahydrocannabinol incorporated in poly(ethylene oxide) matrices," Eur J Pharmceutics and Biopharmaceutics, Oct. 2008, 70(2): 605-614.

Thurman et al., "Standards for epidemiologic studies and surveillance of epilepsy," Epilepsia, Sep. 2011, 52 Suppl 7: 2-26.

Thurstone, "Avoid Charlotte's Web for Epilepsy," Jun. 26, 2014, URL <http://drthurstone.com/charlotted-web-not-safest-option-epiliepsy-treatment/>, 4 pages.

Trembly and Sherman, "Double-blind clinical study of cannabidiol as a secondary anticonvulsant," Marijuana '90 Int. Conf, on Cannabis and Cannabinoids, Kolympari (Crete), Jul. 8-11, 1990, 1 page, Abstract Only.

Turkanis et al., "An Electrophysiological Analysis of the Anticonvulsant Action of Cannabidiol on Limbic Seizures in Conscious Rats," Epilepsia, 1979, 20:351-363.

Unimed Pharmaceuticals, Inc., "Marinol®," Jul. 2006 <https://www.accessdata.fda.gov/drugsatfda_docs/label/2006/018651s025s026lbl.pdl>, 11 pages.

Usami et al., "Synthesis and Pharmacological Evaluation in Mice of Halogenated Cannabidiol Derivatives," Chem Pharm Bull, Nov. 1999, 47(11):1641-1645.

USPTO Decision on Appeal in U.S. Appl. No. 10/318,659 (Appeal 2009-011751), dated Jul. 8, 2010, 23 pages.

USPTO Decision on Appeal in U.S. Appl. No. 13/698,730 (Appeal 2016-006358), dated Jun. 21, 2017, 6 pages.

USPTO Information Disclosure Statement Form PTO-1449 in U.S. Appl. No. 13/380,305, dated Nov. 24, 2014, 8 pages.

USPTO Notice of Allowance in U.S. Appl. No. 13/380,305, dated Dec. 10, 2014, 5 pages.

USPTO Notice of Allowance in U.S. Appl. No. 13/380,305, dated Mar. 19, 2015, 7 pages.

USPTO Office Action in U.S. Appl. No. 13/380,305, dated Aug. 25, 2014, 6 pages.

USPTO Request for Continued Examination with the Amendment and Information Disclosure Statement in U.S. Appl. No. 13/380,305, filed Mar. 2, 2015, 8 pages.

USPTO Third Preliminary Amendment under 37 C.F.R. 1.115 in U.S. Appl. No. 13/380,305, dated May 23, 2014, 4 pages.

Utah.gov [online], "2nd Agenda Controlled Substances Advisory Committee Meeting," Nov. 12, 2013, URL <https://www.utah.gov/pmn/files/81459.pdf>, 63 pages.

Van Rijckevorsel, "Treatment of Lennox-Gastaut Syndrome: overview and recent findings," Neuropsychiatr Dis Treat, Dec. 2008, 4(6): 1001-1019.

Velisek, "Chapter 11: Models of Chemically-Induced Acute Seizures," Models of Seizures and Epilepsy, 2006, 127-152.

Veliskova, "Chapter 48: Behavioral Characterization of Seizures in Rats," Models Seizures Epilepsy, 2006, 601-611.

Vollner et al., "Haschisch XX+ [Haschiscc XX+]: Cannabidivarin, a new hashish substance," Tetrahedron Letters, 1969, 10(3):145-147.

Wahle et al., "Development of Tolerance to the Anticonvulsant Effect of Valproate but not to Ethosuximide in a Rat Model of Absence Epilepsy," Eur J Pharma, May 1990, 181(1-2): 1-8.

Wallace et al., "Assessment of the role of CB1 receptors in cannabinoid anticonvulsant effects," European J Pharmacology, 2001, 428(1):51-57.

Wallace et al., "Pharmacotherapy for Dravet syndrome," Pediatr, Drugs, Jun. 2016, 18:197-208.

Weston et al., "Tetrahydrocannabivarin Exhibits Anticonvulsant Effects in a Piriform Cortical Brain Slice Model of Epileptiform Activity," Proceedings of the British Pharm Society, Dec. 2006, retrieved on Mar. 1, 2017, URL <http://www.pA2online.org/abstract/abstract.jsp?abid=28533>, 1 page, Abstract Only.

Wikipedia.org [online], "Cannabinoid," Wikipedia, Apr. 2003, retrieved on Mar. 1, 2017, URL <https://en.wikipedia.org/wiki/Cannabinoid>, 15 pages.

Wingerchuk, "Cannabis for medical purposes: cultivating science, weeding out the fiction," Lancent, Jul. 2004, 364:315-316.

Yu et al., "Reduced sodium current in GABAergic interneurons in a mouse model of severe myoclonic epilepsy in infancy," Nature Neuroscience, Sep. 2006, 9(9): 1142-1149.

Yuriev, "Endogenic Cannabinoid System is a New Perspective Object of Pharmacotherapeutic Effect to Disease of Nervous System," Ukrainsky Metodichny Chasopis, 2005, 6(50): 21-29 (with English Abstract).

Zhao et al., "Chapter 27: Repetitive Seizures in the Immature Brain," Models of Seizures and Epilepsy, 2006, 341-350.

Zhomitsky and Potvin, "Cannabidiol in Humans—The Quest for Therapeutic Targets," Pharmaceuticals, 2012, 5:529-552.

Zuardi et al., "Cannabidiol, a Cannabis sativa constituent, as an antipsychotic drug," Brazilian Journal of Medicine and Biological Research, Apr. 2006, 39(4): 421-429.

Zuardi et al., "Cannabidiol: from an inactive cannabinoid to a drug with wide spectrum of action," Rev Bras Psiquiatr, 2008, 30(3): 271-80.

AU Re-examination report—standard patent for Australian Patent No. 2012204800, dated May 3, 2019, 7 pages.

Benowitz and Jones, "Cardiovascular and metabolic considerations in prolonged cannabinoid administration in man," J Clin Pharm, 1981, 21: 214S-223S.

Consroe et al., "Controlled clinical trial of cannabidiol in Huntington's Disease," Pharmacology Biochemistiy & Behavior, 1991, 40:701-708.

Curia et al., "The pilocarpine model of temporal lobe epilepsy," J Neuroscience Methods, Jul. 2008, 172(2-4): 143-157.

GB Combined Search and Examination Report in GB Appln. No. GB1621480.1, dated Sep. 22, 2017, pages.

Grotenhermen, "Epilepsiebehandlung des Angelman-Syndroms mit CBD (Cannabidiol) (Epilepsy treatment of Angelman syndrome with CBD (cannabidiol)," Angelman e.V., Jan. 2015, retrieved on Jun. 7, 2019, URL <http://s8a85e4d6fcfb04b6.jimcontent.com/download/version/1472724876/module/9873059694/name/Epilepsiebehandhmg%20durch%20CBD.pdf>, 8 pages (with Machine translation).

Hill et al., "Cannabidivarin is anticonvulsant in mouse and rat," Br J Pharmacol, Dec. 2012, 167(8):1629-1642.

Karler et al., "The anticonvulsant activity of cannabidiol and cannabinol," Life Science, 1973, 13:1527-1531.

Kruk-Slomka et al., "A comparison of mecamylamine and bupropion effects on memory-related responses induced by nicotine and scopolamine in the novel object recognition test in mice," Pharmacological Reports, Aug. 2014, 66(4): 638-646.

Kurz and Blass, "Use of dronabinol (delta-9-THC) in autism: a prospective single-case-study with an early infantile autistic child," 2010, Cannabinoids, 5(4): 4-6.

LaPrairie et al., "Cannabidiol is a negative allosteric modulator of the cannabidinoid CB1 receptor," British J Pharmacology, 2015, 172(20): 4790-4805.

PCT Interntaional Search Report and Written Opinion in International Appln. No. PCT/GB2017/053735, dated Mar. 14, 2018, 14 pages.

Physician's Desk Reference, 63rd Ed., 2009, 423-431, 2192-2194, 2639-2242, 3019-3022.

Sandyk et al., "Preliminary trial of cannabidiol in Huntington's Disease," Marihuana: An International Research Report, 1988, 157-162.

Thomas et al., "Cannabidiol displays unexpectedly high potency as an antagonist of CB1 and CB2 receptor agonists in vitro," British J Pharmacology, 2007, 150(5): 613-623.

U.S. Department of Health and Human Services, Food and Drug Administration Center for Drug Evaluation and Research (CDER),

(56) References Cited

OTHER PUBLICATIONS

"Guidance for Industry Estimating the Maximum Safe Starting Dose in Initial Clinical Trials for Therapeutics in Adult Healthy Volunteers," Jul. 2005, 30 pages.
Zamberletti et al., "Alterations of prefrontal cortex GABAergic transmission in the complex psychotic-like phenotype induced by adolescent delta-9-tetrahydrocaimabinol exposure in rats," Neurobiology of Disease, Mar. 2014, 63: 35-47.
U.S. Appl. No. 14/579,061, filed Dec. 22, 2014, Benjamin Whalley.
U.S. Appl. No. 15/346,844, filed Nov. 9, 2016, Benjamin Whalley.
U.S. Appl. No. 16/149,983, filed Oct. 2, 2018, Benjamin Whalley.
U.S. Appl. No. 13/380,305, filed Mar. 19, 2012, Benjamin Whalley.
U.S. Appl. No. 13/977,766, filed Jul. 1, 2013, Benjamin Whalley.
U.S. Appl. No. 14/345,968, filed Mar. 20, 2014, Benjamin Whalley.
U.S. Appl. No. 14/741,793, filed Jun. 17, 2015, Geoffrey Guy.
U.S. Appl. No. 15/284,766, filed Oct. 4, 2016, Geoffrey Guy.
U.S. Appl. No. 15/449,084, filed Mar. 3, 2017, Geoffrey Guy.
U.S. Appl. No. 15/449,124, filed Mar. 3, 2017, Geoffrey Guy.
U.S. Appl. No. 15/449,185, filed Mar. 3, 2017, Geoffrey Guy.
U.S. Appl. No. 15/449,204, filed Mar. 3, 2017, Geoffrey Guy.
U.S. Appl. No. 15/449,177, filed Mar. 3, 2017, Geoffrey Guy.
U.S. Appl. No. 15/948,412, filed Apr. 9, 2018, Geoffrey Guy.
U.S. Appl. No. 14/881,954, filed Oct. 13, 2015, Geoffrey Guy.
U.S. Appl. No. 14/881,969, filed Oct. 13, 2015, Geoffrey Guy.
U.S. Appl. No. 15/449,402 filed Mar. 3, 2017, Geoffrey Guy.
U.S. Appl. No. 15/449,535, filed Mar. 3, 2017, Geoffrey Guy.
U.S. Appl. No. 16/198,141, filed Nov. 21, 2018, Geoffrey Guy.
U.S. Appl. No. 14/741,829, filed Jun. 17, 2015, Geoffrey Guy.
U.S. Appl. No. 15/183,947, filed Jun. 16, 2015, Geoffrey Guy.
U.S. Appl. No. 15/519,233, filed Apr. 14, 2017, Geoffrey Guy.
U.S. Appl. No. 15/519,244, filed Apr. 14, 2017, Geoffrey Guy.
U.S. Appl. No. 15/640,033, filed Jun. 30, 2017, Jitinder Wilkhu.
U.S. Appl. No. 15/751,563, filed Feb. 9, 2018, Colin Stott.
U.S. Appl. No. 16/090,039, filed Sep. 28, 2018, Geoffrey Guy.
U.S. Appl. No. 16/314,569, filed Dec. 31, 2018, Harshit Shah.
U.S. Appl. No. 16/328,209, filed Feb. 25, 2019, Colin Stott.
U.S. Appl. No. 16/467,639, filed Jun. 7, 2019, Geoffrey Guy.

[No Author Listed], "Missouri House passes cannabis extract legislation," Kansas City Star, 2014, https://kansascity.com/news/politics-government/article346747.html, 2 pages.
cdc.gov [online], "2 to 20 years: Girls Stature-for-age and Weigh-for-age percentiles," National Center for Health Statistics and National Center for Chronic Disease Prevention and Health Promotion, last modified Nov. 2000, <https://www.cdc.gov/growthcharts/data/set1clinical/cj411022.pdf>, 1 page.
Chou, "Theoretical basis, experimental design, and computerized simulation of synergism and antagonism in drug combination studies," Pharmacol Rev., Sep. 2006, 58(3), 621-681.
Kuhn et al., "Potent activity of carfilzomib, a novel, irreversible inhibitor of the ubiquitin-proteasome pathway, against preclinical models of multiple myeloma," Blood, Nov. 2007, 110(9): 3281-3290.
Morelli et al., "The effects of cannabidiol and its synergism with bortezomib in multiple myeloma cell lines. A role for transient receptor potential Vanilloid type-2," Int J Cancer, Jun. 2014, 134(11):2534-2546.
Nabissi et al, "Cannabinoids synergize with cafilzomib, reducing multiple myeloma cells viability and migration," Oncotarget, Oct. 2016, 7: 77553.
PCT International Preliminary Report on Patentability in International Appln. No. PCT/GB2017/052229, dated Feb. 26, 2019, 7 pages.
PCT International Search Report and Written Opinion in International Appln. No. PCT/GB2017/052229, dated Oct. 6, 2017, 10 pages.
Raab et al., "Multiple myeloma," Lancet, Jul. 2009, 374(9686): 324-339.
Velasco et al., "Anticancer mechanisms of cannabinoids," Curr Oncol, Mar. 2016, 23(2): S23-S32.
Astruc-Diaz, F., "Cannabinoids delivery systems based on supramolecular inclusion complexes and polymeric nanocapsules for treatment of neuropathic pain," Université Claude Bernard—Lyon I, 2012, submitted on Jan. 23, 2014; https://tel.archives-ouvertes.fr/tel-00935588 [accessed Nov. 1, 2019].
Kurz & Blass, "Use of dronabinol (delta-9-THC) in autism: A prospective single-case-study with an early infantile autistic child," Cannabinoids, 5(4):4-6 (2010).

* cited by examiner

PARENTERAL FORMULATIONS

This application is a National Stage application under 35 U.S.C. § 371 of International Application No. PCT/GB2017/051913, having an International Filing Date of Jun. 29, 2017, which claims the benefit of EP Application No. 1611545.3 filed Jul. 1, 2016. This disclosures of the prior applications are considered part of (and are incorporated by reference in) the disclosure of their application.

The present invention relates to parenteral formulations, and more particularly to cannabinoid containing intravenous (IV) formulations.

BACKGROUND TO THE INVENTION

Parenteral formulations, also called injectable formulations, may be used to deliver a drug intravenously, subcutaneously, or intramuscularly. The drug may be formulated as a liquid or it may be lyophilized.

When looking to solubilize an active pharmaceutical ingredient (API) together with excipients to produce an injectable formulation, a formulation chemist would generally follow a structured approach, as set out by e.g. Strickley, Pharmaceutical Research, Vol 21, No 2, 2004 (Table VIII). Thus, depending on the solubility of the API, the skilled person would first look at simple aqueous isotonic solutions and progresses through more complex approaches using: pH control, the addition of co-solvents, the use of pH adjustment in combination with co-solvents, complexation; organic solvent/surfactant combinations for dilution with an aqueous diluent to an oil in water emulsion and ultimately, the use of liposomes.

Thus, an ideal immediate release injectable formulation is aqueous and isotonic with physiological fluids such as saline, dextrose (5%) or lactated Ringer's with a pH of 7.

Where the API is not soluble, the skilled formulation chemist, as outlined above, would look to increase solubility through pH change and/or adding a co-solvent. Typical organic solvents used in IV formulations include ethanol, dimethylacetamide (DMA), glycerin, polyethylene glycol (PEG 300) and propylene glycol. The combination of both pH modification and co-solvent is a very powerful solubilization strategy, and if a drug is not solubilized using such an approach the next step would be to use complexing agents, such as, cyclodextrins. If this doesn't work the drug is considered "challenging" whereupon surfactants are used. Typical surfactants for intravenous infusion formulations include polyethoxylated castor oil e.g. Cremophor EL, PEG-60 Hydrogenated Castor Oil e.g. Cremophor RH60 and polyoxyethylene-sorbitan-20 mono-oleate e.g. Polysorbate 80. When this fails, oil in water emulsions or liposomes are usually the last option. Oil in water emulsions are however rarely used in commercial products.

Cannabinoids are highly lipophilic with the consequence that delivering them efficiently is challenging.

They include cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCVA). This list is not exhaustive and merely details the cannabinoids which are identified in the present application for reference. So far, over 100 different phytocannabinoids have been identified and these cannabinoids can be split into different groups as follows: Phytocannabinoids; Endocannabinoids; and Synthetic cannabinoids.

Approved cannabinoid containing medicines have to date been delivered orally e.g. Nabilone and Dronabinol, or via the oromucosal route e.g. Nabiximols.

IV formulations of cannabinoids have of course been prepared for research purposes, where they can be manufactured for immediate use, but such formulations are not suitable for use as medicines due to e.g. poor stability.

Parenteral formulations of Marijuana constituents are disclosed in the Journal of Pharmaceutical Sciences, Vol 61, No 7, 1106-1112 1972 (incorporated by reference). This document discloses emulsions for parenteral use consisting of (i) sesame oil (10-15%) plus Polysorbate 80 (0.4-1%) in saline containing up to 4% tetrahydrocannabinol or (ii) sesame oil (5-10%), plus polyvinylpyrrolidone (PVP) (4-5%) containing approximately 1% cannabinoid. The document notes that the ratio of emulsifier to cannabinoid proved critical to obtain stable emulsions. The document teaches that aqueous cannabinoid containing systems for parenteral administration must incorporate some type of emulsifier and states the limitations (in formulating cannabinoids) falls into three categories:

(a) The low concentration of cannabinoid achieved dictates the volume of formulation that must be given;
(b) The concentration of emulsifier, and number of treatments, introduce the hazard of vehicle toxicity; and
(c) The lability of the formulation may require frequent preparation of the injectable.

The document goes on to comment on each of these limitations.

More specifically (Table 1 therein) shows the solubility of tetrahydrocannabinol (THC) in a range of solvents, with solubility ranging from 1 g/ml in ethanol to 0.28 g/ml in Polysorbate 80 (a paste).

With reference to the emulsion characteristics, various solvent/emulsifier/diluent combinations were examined. The studies (Table 2 therein) demonstrated that "small" quantities of solubilizer or emulsifier provided stable emulsions, whereas e.g. "relatively high" concentrations of cannabinoid with 10% Polysorbate 80 yielded emulsions which were stable only for a few minutes. It is further stated that small quantities of organic solvents failed to provide suitable cannabinoid suspensions (e.g. propylene glycol and glycerol formed a 2 phase system upon dilution with saline) and the most successful emulsions comprised stock solutions (1 ml) of cannabinoid in sesame oil (100-400 mg/ml) to which Polysorbate 80 and 8-9 ml of isotonic saline were added and emulsified by sonication. Other useable emulsions were obtained with cannabinoid in sesame oil and 5-10% Polyvinylpyrrolidone (PVP) or 1% polyoxalene (stable for 3-6 hours).

The discussion section included a review of various IV formulations used in animal studies. These included sesame oil-saline; propylene glycol; Polysorbate-saline; polyethylene glycol 300 and 10% PVP-saline.

The conclusions were that suspending agents like Polysorbate offered useful aqueous systems, but species sensitivity presented a formidable difficulty, whereas emulsions with natural oils and emulsifiers afford a good approach to injectables for chronic studies.

WO 2016/147186 discloses cannabis based emulsion formulations. It takes a cannabinoid containing oily phase comprising phospholipids and mixes this phase with a water phase, comprising glycerol to form a pre-emulsion which is microfluidised to form a micro-emulsion. The micro-emulsion can be administered by a range of routes including intranasal, transdermal, intravenous, oral, and topical. In contrast, the parenteral formulation of the present invention does not comprise phospholipids and are based on the selection of the given surfactant and isotonic agent together with a stability enhancer.

US 2007/0060638 discloses combination therapies of a cannabinoid receptor agonist and antagonist. It teaches the therapeutic compound may be administered parenterally mentioning dispersions can be prepared in, for example, glycerol, polyethylene glycol and mixtures thereof.

US 2013/0209483 teaches the use of CBD containing pharmaceutical compositions. Amongst many formulations disclosed are injectable formulations. The document teaches using sterile aqueous solutions or dispersions and mentions a number of suitable carriers.

WO 2008/144475 relates to CBD derivatives for treating cancer. It makes reference to various routes of administration, including parenteral. It further mentions the use of various solvents, isotonicity agents, antioxidants and chelating agents.

WO 2008/019146 discloses aqueous dronabinol containing formulations. The formulations are for delivery by a range of techniques. They include on or more co-solvents, typically organic co-solvents such as ethanol or polyethylene glycol, solubilizing agents may be included as may a range of other components including surfactants, antioxidants and isotonicity agents.

The formulation of injectable cannabinoid formulations therefore presents a major challenge to the skilled person. Achieving good solubility, low toxicity and stability cannot be underestimated.

Despite this, the Applicant has developed a stable (non-oil based) aqueous parental cannabinoid containing formulation using surfactants which contain the desired cannabinoid in amounts enabling effective subject dosing in combination with one or more stability enhancers. The stability enhancers include one or more antioxidant(s) and chelating agent(s).

BRIEF SUMMARY OF THE DISCLOSURE

In accordance with a first aspect of the present invention there is provided an aqueous parenteral cannabinoid containing formulation comprising:
(i) a cannabinoid;
(ii) an isotonic agent;
(iii) a surfactant; and
(iv) one or more stability enhancers.

Preferably the cannabinoid is selected from cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCVA).

More preferably still the cannabinoid is CBD or CBDV.

It may be a highly purified natural compound or a synthetically manufactured compound with a purity of greater than 98%, and more preferably still greater than 99%.

For CBD or CBDV, the cannabinoid may be present in the formulation in an amount of from 0.3 to 50 mg/ml, preferably 0.5 to 20 mg/ml, more preferably 1 to 7 mg/ml, and most preferably 3 to 5 mg/ml.

Preferably the isotonic agent is selected from: polyethylene glycol, glycerol, saline, and glucose and are used in amounts to provide an osmolality in the range of, 100-500 mOsMol/Kg, more preferably still, 200-400 mOsMol/Kg, more preferably still 285-310 mOsMol/Kg, and most preferably about 300 OsMol/Kg.

Most preferably the isotonic agent is glycerol and is present in an amount of 5 to 50 mg/ml, more preferably 10-30 mg/ml, and most preferably 20 mg/ml.

If the product is to be freeze dried then a bulking agent such as, mannitol, sucrose, and trehalose may be added.

The preferred surfactant is a non-ionic surfactant. Most preferred are (i) Polyoxyethylene (20) sorbitan monooleate, also called Polysorbate 80 (Tween 80), (ii) Macrogol 15 hydroxystearate which is a mixture of mainly mono esters and di esters of 12-hydroxystearic acid and macrogols obtained by the ethoxylation of 12-hydroxystearic acid. The number of moles of ethylene oxide reacted per mole of 12-hydroxystearic acid is 15. Proprietary versions include Solutol HS15, Crodasol HS and Kolliphor HS 15 and (iii) Polyoxamers which are triblock co-polymers of a central hydrophobic chain of polyoxypropylene flanked by two hydrophilic chains of polyoxyethylene. Proprietary brands include Pluronics.

PVP (K12 or K17) may also be used as a solubiliser.

A most preferred surfactant is Macrogol 15 hydroxystearate (Kolliphor HS15). This may be used in an amount of from 5 to 500 mg/ml, more preferably 10 to 100 mg/ml, and most preferably at about 50 mg/ml.

Preferred stability enhancers comprise one or more antioxidants selected from ascorbic acid, monothioglycerol, cysteine HCl and Glutathione.

Particularly preferred is ascorbic acid which may be used in amounts of from 0.5 to 10 mg/ml, more preferably 1 to 5 mg/ml, and most preferably about 2 mg/ml.

Alternatively, monothioglycerol may be used, also in an amount of from 0.5 to 10 mg/ml, more preferably 1 to 5 mg/ml, and most preferably about 2 mg/ml.

It is most preferable to use monothioglycerol and ascorbic acid in combination in the amounts indicated above for each anti-oxidant.

Preferably the stability enhancers comprise, in addition to antioxidants, a chelating agent from disodium EDTA and calcium disodium EDTA. These are preferably used in amounts of from 0.1 to 10 mg/ml, more preferably 0.5 to 5 mg/ml, and most preferably about 1 mg/ml.

Preferably the formulation has a pH between 3 and 6, most preferably about 4.

The formulation may take the form of a bolus formulation or an infusion formulation which may be diluted in use with, for example an isotonic glucose solution.

The preferred formulations preferably provide a shelf life of at least 12 months without refrigeration, more preferably 18 months without refrigeration and most preferably still 24 months without refrigeration.

The preferred formulations are most preferably stable in climatic zones I and II for up to 18 months at 25° C., and stable in climatic zones III and IV for up to 12 months at 30° C.

The formulation may be packaged for use in a vial, ampule, syringe, infusion bag or other container.

The formulation should be sterile and may be sterilised by filtration.

The term "about" is defined according to the invention as meaning plus or minus 10% of the amount stated.

According to a second aspect of the present invention there is provided a method of preparing an aqueous parenteral cannabinoid according to the invention comprising preparing a stock solution of a cannabinoid in a surfactant;

preparing an aqueous solution comprising the isotonic agent and one or more stability enhancers; and slowly adding the aqueous solution to the stock solution of the cannabinoid in the surfactant.

Preferably the cannabinoid is CBD or CBDV, the surfactant is macrogol 15 hydroxystearate, the isotonic agent comprises glycerol, and the stability enhancers are ascorbic acid, monothioglycerol and calcium disodium EDTA.

Preferably the Macrogol 15 hydroxystearate is heated to about 40° C., and CBD or CBDV is added at about 60° C.; the water is sparged with nitrogen, heated to about 60° C. and glycerol, monothioglycerol, EDTA and ascorbic acid added; and then the resulting aqueous solution is slowly added to the solution of CBD or CBDV in Macrogol 15 hydroxystearate.

The resulting formulation is sterilized by filtration and the formulation is aseptically filled into a vial, ampule, syringe, infusion bag or other container.

This may be performed in a 4-glove general purpose filling isolator under nitrogen.

In accordance with a third aspect of the present invention there is provided a method of treating a subject comprising administering an aqueous parenteral cannabinoid formulation according to the invention.

Preferably the aqueous parenteral cannabinoid formulation is delivered by injection. Preferably the subject is a human.

The aqueous parenteral cannabinoid formulation is for use as a rescue formulation. Preferably the rescue medication is for use as a neuroprotectant or anti-convulsive.

The rescue medication may be used to treat newborn hypoxic-ischemic encephalopathy (NHIE), status epilepticus or stroke.

In a fourth aspect of the present invention there is provided an aqueous parenteral cannabinoid formulation according to the invention for use in the treatment of conditions requiring the administration of a neuroprotectant or anti-convulsive medication.

Preferably the aqueous parenteral cannabinoid formulation is used in the treatment of newborn hypoxic-ischemic encephalopathy (NHIE), status epilepticus or stroke.

DETAILED DESCRIPTION

Embodiments of the invention are further described hereinafter with reference to the following Examples and experiments. Initial investigations focused on CBD as a model cannabinoid and assessed a range of solvents or diluents alone or in combination with surfactants.

The solvents/diluents/surfactants investigated in a solubility screening study are set out in Table 1 below:

TABLE 1

| Excipient |
|---|
| t-butyl alcohol (≤99%) |
| Ethanol (99.8%) |
| Glycerol (99.0-100%) |
| Glucose (99.5%) |
| Mannitol (Pearlitol PF) |
| Macrogol 15 Hydroxystearate Solutol HS15 (Kolliphor HS15) |
| Macrogol 15 Hydroxystearate, Super refined Crodasol HS HP-SO-(MH) |
| PEG 400 (GPR RECTAPUR) |
| Povidone K12 (PF) |
| Povidone K17 (PF) |
| Sodium Chloride (GPR RECTAPUR) |
| Sucrose (≤99.5%) |
| Synperonic PE/F68 Flakes, super refined |

TABLE 1-continued

| Excipient |
|---|
| Trehalose (≤99%) |
| Tween 80-LQ-(Cqq), super refined |

The methodology for the solubility screening was as follows:

Solubility Screening 8 mg of API (CBD) was weighed into a 2 ml clear glass vial and 0.5 or 1 ml of solution was added. All the vials were sonicated for 5 minutes and then left on a roller mixer, mixing for 48 hours. The roller mixer was covered with aluminium foil to prevent light exposure.

After 24 hours, the vials which showed good API solubility visually (i.e. no solid seen) had more API added and this process was repeated until the samples were saturated or ceased, if saturation condition could not be met after adding a substantial amount of API.

After 48 hours, all samples were centrifuged, and the supernatants taken (250 or 500 μL) using a Gilson pipette and added into a 10 ml volume flask. Methanol was used to make up the volume and the samples were tested by HPLC. Sample numbers 5, 9 and 10 were assayed using visual observation as the amount of API that could be added was so high.

The assay results are shown in Table 2 below:

TABLE 2

| Sample No. | Sample ID | ASSAY CBD (mg/ml) |
|---|---|---|
| 1 | ETOH (0.5% v/v) | 0.0496 |
| 2 | ETOH (1% v/v) | 0.0426 |
| 3 | ETOH (3% v/v) | 0.0054 |
| 4 | ETOH (5% v/v) | 0.0244 |
| 5* | ETOH (100% v/v) | >1000 |
| 6 | PEG400 (5% v/v) | 0.1596 |
| 7 | PEG400 (15% v/v) | 0.1946 |
| 8 | PEG400 (25% v/v) | 0.1617 |
| 9* | PEG400 (100% v/v) | >400 |
| 10* | t-butyl alcohol (TBA), (100% v/v) | >600 |
| 11 | Glycerol (10% v/v) | 0.0029 |
| 12 | Glycerol (20% v/v) | 0.0437 |
| 13 | Glycerol (40% v/v) | 0.0859 |
| 14** | Glycerol (100% v/v) | — |
| 15 | Saline (0.45% w/v) | 0.0021 |
| 16 | Saline (0.9% w/v) | 0.0551 |
| 17 | Glucose (5% w/v) | 0.0008 |
| 18 | Glucose (10% w/v) | 0.2379 |
| 19 | Mannitol (5% w/v) | 0.0009 |
| 20 | Mannitol (10% w/v) | 0.0148 |
| 21 | Sucrose (5% w/v) | 0.0202 |
| 22 | Sucrose (10% w/v) | 0.0822 |
| 23 | Trehalose (10% w/v) | 0.0124 |
| 24 | Trehalose (5% w/v) | 0.0600 |
| 25 | Polysorbate 80 (0.5% w/v) | 3.2600 |
| 26 | Polysorbate 80 (1% w/v) | 6.0415 |
| 27 | Polysorbate 80 (3% w/v) | 22.9779 |
| 28 | Polysorbate 80 (5% w/v) | 30.6529 |
| 29 | Crodosal HS (0.5% w/v) | 2.6529 |
| 30 | Crodosal HS (1% w/v) | 5.4462 |
| 31 | Crodosal HS (2% w/v) | 5.0344 |
| 32 | Crodosal HS (3% w/v) | 6.3465 |
| 33 | Crodosal HS (4% w/v) | 7.5569 |
| 34 | Crodosal HS (5% w/v) | 7.9983 |
| 35 | Pluronic F68 (1% w/v) | 0.1403 |
| 36 | Pluronic F68 (2% w/v) | 0.5209 |
| 37 | Pluronic F68 (3% w/v) | 0.5042 |
| 38 | Pluronic F68 (5% w/v) | 1.0654 |
| 39 | PVP K12 (1% w/v) | 0.0615 |
| 40*** | PVP K12 (2% w/v) | 0.1746 |
| 41 | PVP K12 (3% w/v) | 0.0639 |

TABLE 2-continued

| Sample No. | Sample ID | ASSAY CBD (mg/ml) |
|---|---|---|
| 42 | PVP K12 (5% w/v) | 0.0157 |
| 43 | PVP K17 (1% w/v) | 0.0031 |
| 44 | PVP K17 (2% w/v) | 0.0433 |
| 45 | PVP K17 (3% w/v) | 0.0409 |
| 46 | PVP K17 (5% w/v) | 0.2360 |

*Solubility data acquired by visual observation (all the others were acquired by HPLC).
**Sample not tested because of sampling problem.
***High assay result probably due to sampling problem.

According to the solubility results, ethanol (100%), PEG400 (100%) and TBA (100%) showed the highest solubility for CBD. Polysorbate 80 (Tween) and Crodosal HS, at all concentrations tested, also showed better solubility compared to the other solutions tested. The use of Pluronic F68 also gave solubility improvement to CBD to a limited extent. The solubility of CBD in solutions containing different bulking agents such as sucrose, mannitol and trehalose was also investigated. Very limited solubility improvement was noticed. Saline (0.45% and 0.9%) and Glucose (G5 and G10) solutions were tested. Better solubility of CBD was seen in Glucose G10. Two polymers (PVP K12 and K17) were tested. A slight solubility improvement was seen. A linear relation of solubility and PVP concentration was observed for PVP K17 solutions; however, this linearity was not seen in PVP K12 (it should be noted that a sampling problem might have happened during measurement of sample 40 during HPLC analysis). TBA showed good CBD solubility in this study which suggests it could be used as a potential solvent for a lyophilised formulation.

It was observed that whilst pure ethanol and PEG400 resulted in the highest solubility of CBD, the aqueous solutions containing different amount of ethanol and PEG400 did not result in high CBD solubility. Even though the amount of PEG400 and ethanol was increased to 50% in water, the 10 mg of CBD added did not dissolve completely. This phenomenon was probably due to the poor aqueous solubility of CBD.

Based upon the above, Applicant selected a Macrogol 15 hydroxystearate as the preferred surfactant, and investigated the effect of different antioxidants, chelating agents and isotonic agents on short term stability (1 week, 2 week and 1 month).

A number of test formulations are illustrated in Table 3 below:

TABLE 3

| Sample No | CBD (mg/ml) | Solutol HS15 (% w/v) | NaCl (% w/v) | Glucose (% w/v) | Glycerol (% w/v) | Disodium EDTA (% w/v) | Ascorbic acid (% w/v) | Mono-thioglycerol (% w/v) | Cysteine HCl (% w/v) | Glutathione (% w/v) |
|---|---|---|---|---|---|---|---|---|---|---|
| 1 | 5 | 5 | — | — | — | — | — | — | — | — |
| 2 | 5 | 5 | — | 5 | — | 0.2 | 1 | — | — | — |
| 3 | 5 | 5 | — | 5 | — | 0.2 | — | 1 | — | — |
| 4 | 5 | 5 | — | 5 | — | 0.2 | — | — | 0.5 | — |
| 5 | 5 | 5 | — | 5 | — | 0.2 | — | — | — | 0.5 |
| 6 | 5 | 5 | — | 5 | — | 0.2 | 1 | 1 | — | — |
| 7 | 5 | 5 | — | — | 20 | 0.2 | 1 | — | — | — |
| 8 | 5 | 5 | — | — | 20 | 0.2 | — | 1 | — | — |
| 9 | 5 | 5 | — | — | 20 | 0.2 | — | — | 0.5 | — |
| 10 | 5 | 5 | — | — | 20 | 0.2 | — | — | — | 0.5 |
| 11 | 5 | 5 | — | — | 20 | 0.2 | 1 | 1 | — | — |
| 12 | 5 | 5 | 0.9 | — | — | — | — | — | — | — |

The relative chemical stability of these formulations are shown in Tables 4 (CBD) and 5 (placebo) below which show respectively the stability of CBD as an assayed % and as a % impurity.

TABLE 4

| | | T0 | | T1w | | T2w | | T1m | | |
|---|---|---|---|---|---|---|---|---|---|---|
| Formulation | CBD (mg/ml) | Assay (mg/ml) | % Assay | Assay (mg/ml) | % Assay | Assay (mg/ml) | % Assay | Assay (mg/ml) | % Assay | Appearance |
| 1 | 5.00 | 4.94 | 98.83 | 4.87 | 99.00 | 4.79 | 95.79 | 4.76 | 95.11 | Clear |
| 2 | 5.00 | 4.98 | 99.55 | 5.00 | 100.01 | 4.96 | 99.17 | 5.03 | 100.55 | Brown |
| 3 | 5.00 | 5.03 | 100.51 | 4.95 | 99.09 | 4.72 | 94.31 | 4.50 | 89.96 | Clear |
| 4 | 5.00 | 4.88 | 97.66 | 4.88 | 97.62 | 4.91 | 98.18 | 4.96 | 99.25 | Turbid |
| 5 | 5.00 | 5.00 | 100.10 | 4.95 | 99.04 | 5.00 | 100.10 | 5.03 | 100.63 | Clear |
| 6 | 5.00 | 5.03 | 100.58 | 4.92 | 98.43 | 4.72 | 94.32 | 4.46 | 89.12 | Clear |
| 7 | 5.00 | 4.82 | 96.44 | 5.09 | 101.86 | 4.91 | 98.92 | 4.93 | 98.60 | Brown |
| 8 | 5.00 | 4.90 | 97.96 | 5.08 | 101.52 | 4.69 | 93.74 | 4.50 | 90.07 | Clear |
| 9 | 5.00 | 4.89 | 97.77 | 5.08 | 101.55 | 5.15 | 103.06 | 4.98 | 99.58 | Turbid |
| 10 | 5.00 | 4.99 | 99.81 | 5.02 | 100.32 | 5.09 | 101.83 | 4.96 | 99.19 | Clear |
| 11 | 5.00 | 4.91 | 98.29 | 4.93 | 98.68 | 4.90 | 97.35 | 4.95 | 98.27 | Clear |
| 12 | 5.00 | 4.88 | 97.69 | 4.12 | 82.40 | 3.98 | 79.64 | 3.28 | 65.67 | Clear |

TABLE 5

| Formulation | T0 Impurity ≤0.045% | T0 Total impurity | T1w Impurity ≤0.045% | T1w % Total impurity | T2w Impurity ≤0.045% | T2w % Total impurity | T1m Impurity ≤0.045% | T1m % Total impurity |
|---|---|---|---|---|---|---|---|---|
| Std | 0.53 | 0.67 | 0.77 | 0.89 | 0.55 | 0.72 | 0.46 | 0.57 |
| 1 | 0.81 | 1.03 | 3.67 | 3.81 | 3.39 | 3.54 | 5.92 | 5.96 |
| 2 | 0.57 | 0.78 | 0.49 | 0.61 | 0.85 | 0.96 | 1.00 | 1.17 |
| 3 | 0.54 | 0.76 | 3.03 | 3.11 | 2.66 | 2.75 | 10.87 | 10.89 |
| 4 | 0.52 | 0.74 | 0.82 | 1.04 | 1.4 | 1.81 | 1.86 | 1.93 |
| 5 | 0.46 | 0.71 | 0.54 | 0.67 | 1.21 | 1.4 | 0.61 | 0.73 |
| 6 | 2.91 | 3.06 | 8.99 | 9.09 | 8.38 | 8.56 | 15.6 | 15.63 |
| 7 | 0.46 | 0.7 | 0.47 | 0.57 | 1.18 | 1.37 | 0.57 | 0.68 |
| 8 | 0.46 | 0.74 | 1.58 | 1.74 | 3.96 | 4.11 | 9.25 | 9.3 |
| 9 | 0.47 | 0.74 | 0.82 | 1.06 | 1.16 | 1.41 | 1.81 | 1.85 |
| 10 | 1.89 | 2.16 | 0.46 | 0.6 | 1.48 | 1.59 | 8.54 | 0.64 |
| 11 | 1.82 | 2.07 | 0.47 | 0.59 | 1.08 | 1.25 | 0.56 | 0.62 |
| 12 | 0.47 | 0.77 | 11.67 | 11.92 | 17.56 | 17.6 | 25.69 | 25.73 |

The results show the best formulations are formulations 2, 4, 5, 7, 9, 10 and 11.

According to the HPLC data, the formulations containing the antioxidants: ascorbic acid, cysteine HCl, and glutathione showed better assay and impurity results after 1 month at 40° C. and 75% relative humidity (RH) compared to the control formulations (1, 12). The formulations 3, 6 and 8, (except for 11, which also contained ascorbic acid) containing monothioglycerol alone degraded significantly compared to the control formulation 1.

Formulation 12 which contained NaCl (as the isotonicity agent) showed the poorest stability with an assay of ~66% and total impurity of ~26%.

The physical stability of the formulations was also studied. The physical appearance of the active samples after storage at 40° C. and 75% RH was also monitored and the results are illustrated in Table 4. It will be noted that Formulations 2 and 7 (containing ascorbic acid alone) turned brown in colour after 1 month at 40° C. and 75% RH. These formulations were however not purged with nitrogen. This browning effect may however be due to the oxidation of the ascorbic acid itself. In contrast, Formulation 6 and 11, which contained ascorbic acid together with monothioglycerol did not discolour. Therefore there appears to be a positive protective effect seen when monothioglycerol is used in combination with ascorbic acid.

The active formulations 2 and 7 which contained ascorbic acid only did not change colour after 1 month at 40° C. and 75% RH which was probably because they were purged with $N_2$ for storage. This demonstrates the importance of a $N_2$ headspace environment in preventing oxidation. Formulation 12 turned yellow after storage while the placebo one remained clear after storage at the same condition. This indicates that this change of colour was associated with the existence of CBD with NaCl.

Both placebos and active formulations 4 and 9 became turbid after storage, which was due to the precipitation of the cysteine HCl.

A summary of the physical appearance of all placebo and active samples is shown in Table 6.

TABLE 6

| Sample | Placebo 40/75 | Active fridge | Active 40/75 |
|---|---|---|---|
| 1 | Clear | Clear - off yellow | Clear - yellow |
| 2 | Brown yellow | Precipitation | Brown yellow |
| 3 | Clear | Clear - off pink | Clear |
| 4 | Turbid | Turbid | Turbid |
| 5 | Clear | Clear - off yellow | Clear - off yellow |
| 6 | Clear | Clear - off pink | Clear |
| 7 | Brown yellow | Clear - off yellow | Brown yellow/hazy |
| 8 | Clear | Clear - off pink | Clear to hazy |
| 9 | Turbid | Hazy | Hazy |
| 10 | Clear | Clear - off yellow | Hazy |
| 11 | Clear | Clear - off yellow | Hazy |
| 12 | Clear | Clear - yellow | Clear - yellow |

A summary of both the chemical and physical stability of the active formulations is shown in Table 7.

TABLE 7

| Formulation | Assay (mg/ml) | % Assay | Impurity ≤0.045% | % Total Impurity | Physical appearance |
|---|---|---|---|---|---|
| 1 | 4.76 | 95.11 | 5.92 | 5.96 | Clear - yellow |
| 2 | 5.03 | 100.55 | 1.09 | 1.17 | Brown yellow |
| 3 | 4.5 | 89.96 | 10.87 | 10.89 | Clear |
| 4 | 4.96 | 99.25 | 1.88 | 1.93 | Turbid |
| 5 | 5.03 | 100.62 | 0.61 | 0.73 | Clear - off yellow |
| 6 | 4.46 | 89.12 | 15.6 | 15.63 | Clear |
| 7 | 4.93 | 98.5 | 0.57 | 0.68 | Brown yellow/hazy |
| 8 | 4.5 | 90.07 | 9.25 | 9.3 | Clear to hazy |
| 9 | 4.96 | 99.58 | 1.81 | 1.86 | White hazy |
| 10 | 4.96 | 99.19 | 0.58 | 0.64 | White hazy |
| 11 | 4.91 | 98.27 | 0.56 | 0.62 | White hazy |
| 12 | 3.28 | 65.67 | 25.69 | 20.79 | Clear - yellow |

Conclusions

Macrogol 15 Hydroxystearate (e.g. Solutol HS15) as a surfactant was very effective at improving the solubility of CBD in water.

A number of antioxidants significantly improved the chemical stability of the formulations. The use of glutathione alone or ascorbic acid and monothioglycerol exhibit significantly improved both chemical and physical stability. Cysteine HCl also showed good chemical stability, however, precipitation of cysteine HCl was seen after storage.

Glycerol and glucose, but not sodium chloride, appeared to be the best isotonicity agents.

Based on the above the Applicant sought to optimise Formulation 11, with the intent of using the lowest amounts of stabilizing excipients to obtain a cannabinoid containing formulation with on osmolarity of approximately 300 mOsMol/Kg (range 200 to 400) exhibiting long term stability testing (1 year plus) without refrigeration. The optimized formulation is shown in Example 1.

Example 1: Optimised Formulation

Table 8 below illustrates the most preferred formulation where the API is cannabidiol (CBD).

TABLE 8

| Product/Raw material | Generic | Broad range | Intermediate range | Quantity |
|---|---|---|---|---|
| CBD or CBDV | Cannabinoid | 0.3-50 | 1-7 | 3 mg/mL (CBD) or 5 mg/mL (CBDV) |
| Macrogol 15 hydroxystearate Ph Eur (Kolliphor HS15) | Surfactant | 5-500 | 10-100 | 50 mg/mL |
| Glycerol Ph Eur | Isotonic agent | 5-50 | 10-30 | 20 mg/mL |
| Sodium calcium edetate Ph Eur | Stability enhancer | 0.1-10 | 0.5-5 | 1 mg/mL |
| Ascorbic acid Ph Eur | Stability enhancer | 0.5-10 | 1-5 | 2 mg/mL |
| 1-Thioglycerol USP | Stability enhancer | 0.5-10 | 1-5 | 2 mg/mL |
| Water for Injection Ph Eur (1000 mL sterile pack) | Solvent | Q.S to volume | Q.S to volume | Q.S to volume |

Method of Manufacture

The preferred formulation (Table 8 above) was prepared as per the steps indicated below:
1. Heat Kolliphor HS15 to about 40° in an oven;
2. Heat water to 60° C. in an oven;
3. Weigh required amount of Kolliphor HS15 into a first container, ensuring no solidification of the Kolliphor HS15 occurs. Add CBD and stir maintaining a temperature of 60° C. Place back in the oven;
4. In a second container weigh the required amount of Glycerol and monothioglycerol. Add 25% of the final volume of pre heated water;
5. Then add the calcium disodium EDTA and ascorbic acid. Mix until fully dissolved then place back in the oven at 60° C.
6. Add the content of the second container drop by drop to the first container whilst constantly stirring to prevent solidification; and
7. Q-s to volume using desired vessel and mix without introduction of bubbles and air.

The formulation may then be spray dried or lyophilized such that it may be stored for a longer period. Such spray dried formulations could then be rehydrated with a sugar solution in order to provide the formulation in a different administration form or as a parenteral formulation.

The formulation of Example 1 was subjected to long term stability testing as set out in Experiment 1 below:

Experiment 1—Long Term Stability Study

This stability study was conducted on 1 batch of the IV formulation. The batch used was manufactured using a 1 L pilot scale manufacture and batch size, at GW Pharma Ltd. The batch was sub-divided (batches A-E, Table 9) to provide sufficient samples for the different storage conditions and time-points. A placebo in a clear glass vial was put alongside this study.

TABLE 9

| Batch | Description |
|---|---|
| A | Type I clear glass vial nitrogen purged (Active) |
| B | Type I amber glass vial nitrogen purged (Active) |
| C | Type I clear glass vial NO nitrogen purge (Active) |
| D | Type I amber glass vial NO nitrogen purge (Active) |
| E | Type I clear glass vial nitrogen purged (Placebo) |
| F (CBDV) | Type I clear glass vial nitrogen purged (Active) |

The objective was to assess the long term stability (at least 12 months) of the formulation. Stoppers were gamma irradiated as per sterile manufacture and all vials containing the formulation were inverted and stored at different storage conditions (temperature and humidity—as per Table 10) to determine whether any potential extractables or leachables were present. The study stressed the formulation at 60° C. to accelerate any possible extractables or leachables that may occur.

TABLE 10

| |
|---|
| 5 ± 3° C. |
| 25 ± 2° C., 60% RH |
| 30 ± 2° C., 65% RH |
| 40 ± 2° C., 75% RH |

Results

Batch A—all Temperatures

Overall throughout the 24 month study period there was no significant decrease in CBD content or pH of the samples as illustrated in Table 11. The formation of the degradant OH-CBD over various temperature and humidity conditions can be considered as an increasing trend of temperature as the results demonstrate that the increase in temperature 5-30° C. over 24 months is causing an increase in OH-CBD formation.

The degradants are below the acceptable limit. In terms of any extractables and leachables from the product stored inverted, there has been no detection or any anomalous peaks forming.

Batch A includes a nitrogen headspace sparge and the use of a clear glass vial and demonstrates acceptable stability over time.

Batch B—all Temperatures

Batch B has been tested to determine any differences between amber glass and clear glass vials and the results are shown in Table 12. The data showed no degradation or significant differences between storing in amber or clear glass vials.

Batch C—all Temperatures

Batch C has been tested at the same intervals as Batch A to determine any differences between nitrogen headspace sparging of the IV product and the results are shown in Table 13. A basic visual appearance test shows significant differences where batch C at the 6 month time point at 30° C. and 40° C. is it shows a yellowing of the solution which is also evident at the 9 and 12 month timepoint. Furthermore with the increase in temperature, 5-40° C. over 6 months, there is a decrease in the pH to <4. Furthermore as the temperature increases there is a rapid rise in the formation of OH-CBD compared to batch A which has had the nitrogen headspace sparge. A glance at the chromatography has also shown that all temperatures within Batch C have very rough baselines and degradation products are more prevalent than in Batch A suggesting that a headspace sparge is required for the stability of this product.

Batch D—all Temperatures

Batch D has been tested at the to determine any differences between amber glass and clear glass vials without the nitrogen headspace sparge in addition to comparing it to the corresponding purged sample in batch B. The results are shown in Table 14. The data shows that non-sparging the formulation, even within an amber glass vial, results in an increase in degradation. In general an overall trend comparing actives containing a nitrogen sparge maintains the pH of the solution >4 units compared to non-sparging which results in the pH decreasing <4 units.

Batch E—all Temperatures

Batch E has been tested at the same intervals as Batch A and C to determine any placebo effects and interferences if any to the active IV product. The results are shown in Table 15. The placebo profile shows no degradation products. However increasing temperature from 5-40° C. results in the pH falling below 4. The placebo (Batch E) at 40° C. at the 6 month time point has shown cloudiness suggesting that the active (Batch A and C) is potentially stabilising the placebo formulation. Furthermore, at the 5° C. condition the 12 month timepoint shows placebo formulation showing cloudiness, which is not observed in Batch A or C at the 5° C. condition.

CBDV—all Temperatures

Overall throughout the 12 month study period there was no significant decrease in CBDV content or pH of the samples as illustrated in Table 16. The formation of the degradant OH-CBDV or THCV over various temperature and humidity conditions can be considered as an increasing trend of temperature as the results demonstrate that the increase in temperature 5-40° C. over 12 months is causing an increase in degradant formation.

Extrapolation to 18 months shows that the degradants will still be below the acceptable limit. In terms of any extractables and leachables from the product stored inverted, there has been no detection or any anomalous peaks forming.

TABLE 11

| Test | Acceptance criteria | Comments (Batch A) | | | | |
|---|---|---|---|---|---|---|
| | | Initial | 5° C. (12 months) | 25° C. (12 months) | 30° C. (12 months) | 40° C. (12 months) |
| Appearance of Solution | Clear solution free from particulates | Complies | Complies | Complies | Complies | Complies |
| pH | >3.5 | 4.04 | 4.01 | 4.08 | 3.95 | 4.13 |
| CBD Content (%) | Within ±3% of initial | 100.0 | 100.6 | 101.1 | 101.3 | 102.3 |
| Degradants (% of CBD content) | | | | | | |
| CBE I | NMT 1.0% | 0.00 | 0.00 | 0.00 | 0.00 | 0.04 |
| OH-CBD | NMT 1.0% | 0.05 | 0.05 | 0.09 | 0.14 | 0.25 |
| Individual unspecified degradants | Monitor Above 0.1% | RRT 1.90: 0.08 | RRT 1.90: 0.08 | RRT 1.90: 0.09 | RRT 1.90: 0.11 | RRT 1.90: 0.17 |
| Odour | For Information Only | Sulphurous/egg smell | A faint sulphurous smell | A sulphurous smell | A sulphurous smell | A faint sulphurous smell |

| Test | Acceptance criteria | Comments (Batch A) | | | |
|---|---|---|---|---|---|
| | | Initial | 5° C. (24 months) | 25° C. (24 months) | 30° C. (24 months) |
| Appearance of Solution | Clear solution free from particulates | Complies | Complies | Complies | Complies |
| pH | >3.5 | 4.04 | 3.94 | 4.02 | 3.85 |
| CBD Content (%) | Within ±3% of initial | 100.0 | 97.6 | 97.3 | 96.8 |
| Degradants (% of CBD content) | | | | | |
| CBE I | NMT 1.0% | 0.00 | 0.00 | 0.00 | 0.00 |
| OH-CBD | NMT 1.0% | 0.05 | 0.00 | 0.01 | 0.14 |
| Individual unspecified degradants | Monitor Above 0.1% | RRT 1.90: 0.08 | RRT 1.90: 0.08 | RRT 1.90: 0.09 | RRT 1.90: 0.11 |
| Odour | For Information Only | Sulphurous/egg smell | A sulphurous smell | A sulphurous smell | A sulphurous smell |

TABLE 12

| Test | Acceptance criteria | Comments (Batch B) | | | | |
|---|---|---|---|---|---|---|
| | | Initial | 5° C. (12 months) | 25° C. (12 months) | 30° C. (12 months) | 40° C. (12 months) |
| Appearance of Solution | Clear solution free from particulates | Complies | Complies | Complies | Complies | Cloudy colourless solution |
| pH | >3.5 | 4.04 | 3.89 | 3.90 | 4.05 | 4.05 |
| CBD Content (%) | Within ±3% of initial | 100.0 | 99.5 | 99.5 | 100.1 | 100.3 |
| Degradants (% of CBD content) | | | | | | |
| CBE I | NMT 1.0% | 0.00 | 0.00 | 0.00 | 0.00 | 0.00 |
| OH-CBD | NMT 1.0% | 0.07 | 0.05 | 0.09 | 0.13 | 0.24 |
| Individual unspecified degradants | Monitor Above 0.1% | RRT 1.90: 0.07 | RRT 1.90: 0.03 | RRT 1.90: 0.07 | RRT 1.90: 0.09 | RRT 1.90: 0.13 |
| Odour | For Information Only | Sulphurous/egg smell | A sulphurous smell | A sulphurous smell >5° C. | A sulphurous smell | A sulphurous smell |

| Test | Acceptance criteria | Comments (Batch B) | | | |
|---|---|---|---|---|---|
| | | Initial | 5° C. (24 months) | 25° C. (24 months) | 30° C. (24 months) |
| Appearance of Solution | Clear solution free from particulates | Complies | Complies | Complies | Complies |
| pH | >3.5 | 4.04 | 3.89 | 3.85 | 4.12 |
| CBD Content (%) | Within ±3% of initial | 100.0 | 97.4 | 97.9 | 98.2 |
| Degradants (% of CBD content) | | | | | |
| CBE I | NMT 1.0% | 0.00 | 0.00 | 0.00 | 0.00 |
| OH-CBD | NMT 1.0% | 0.05 | 0.00 | 0.01 | 0.1 |
| Individual unspecified degradants | Monitor Above 0.1% | RRT 1.90: 0.08 | RRT 1.90: 0.08 | RRT 1.90: 0.09 | RRT 1.90: 0.11 |
| Odour | For Information Only | Sulphurous/egg smell | A sulphurous smell | A sulphurous smell | A sulphurous smell |

TABLE 13

| Test | Acceptance criteria | Comments (Batch C) | | | | |
|---|---|---|---|---|---|---|
| | | Initial | 5° C. (12 months) | 25° C. (12 months) | 30° C. (12 months) | 40° C. (12 months) |
| Appearance of Solution | Clear solution free from particulates | Complies | Complies | Complies | Clear faint yellow liquid | Cloudy yellow solution |
| pH | >3.5 | 4.05 | 3.95 | 3.81 | 3.82 | 3.79 |
| CBD Content (%) | Within ±3% of initial | 100.0 | 101.2 | 100.9 | 100.1 | 97.3 |
| Degradants (% of CBD content) | | | | | | |
| CBE I | NMT 1.0% | 0.00 | 0.00 | 0.02 | 0.03 | 0.26 |
| OH-CBD | NMT 1.0% | 0.07 | 0.06 | 0.11 | 0.15 | 0.37 |
| Individual unspecified degradants | Monitor Above 0.1% | RRT 1.90: 0.06 | RRT 1.90: 0.08 | RRT 1.90: 0.06 | RRT 1.90: 0.12 | RRT 1.90: 0.21 RRT 1.97: 0.13 |
| Odour | For Information Only | Sulphurous/egg smell | A sulphurous smell | A sulphurous smell | A sulphurous smell >25° C. | A sulphurous smell |

| Test | Acceptance criteria | Comments (Batch C) | | | |
|---|---|---|---|---|---|
| | | Initial | 5° C. (24 months) | 25° C. (24 months) | 30° C. (24 months) |
| Appearance of Solution | Clear solution free from particulates | Complies | Complies | Complies | Complies |
| pH | >3.5 | 4.04 | 3.88 | 3.85 | 3.83 |
| CBD Content (%) | Within ±3% of initial | 100.0 | 97.0 | 95.8 | 95.2 |
| Degradants (% of CBD content) | | | | | |
| CBE I | NMT 1.0% | 0.00 | 0.00 | 0.00 | 0.00 |
| OH-CBD | NMT 1.0% | 0.05 | 0.00 | 0.01 | 0.14 |
| Individual unspecified degradants | Monitor Above 0.1% | RRT 1.90: 0.08 | RRT 1.90: 0.08 | RRT 1.90: 0.09 | RRT 1.90: 0.11 |
| Odour | For Information Only | Sulphurous/egg smell | A sulphurous smell | A sulphurous smell | A sulphurous smell |

TABLE 14

| Test | Acceptance criteria | Comments (Batch D) | | | | |
|---|---|---|---|---|---|---|
| | | Initial | 5° C. (12 months) | 25° C. (12 months) | 30° C. (12 months) | 40° C. (12 months) |
| Appearance of Solution | Clear solution free from particulates | Complies | Complies | Complies (yellow solution) | Complies (yellow solution) | Cloudy, yellow solution free from particulates |
| pH | >3.5 | 4.05 | 3.82 | 3.69 | 3.71 | 3.74 |
| CBD Content (%) | Within ±3% of initial | 100.0 | 100.1 | 100.6 | 100.1 | 97.0 |
| Degradants (% of CBD content) | | | | | | |
| CBE I | NMT 1.0% | 0.00 | 0.00 | 0.04 | 0.07 | 0.17 |
| OH-CBD | NMT 1.0% | 0.07 | 0.06 | 0.12 | 0.17 | 0.43 |
| Individual unspecified degradants | Monitor Above 0.1% | RRT 1.90: 0.06 RRT 0.46: 0.03 | RRT 1.90: 0.07 | RRT 1.90: 0.08 | RRT 1.90: 0.09 | RRT 1.90: 0.24 |
| Odour | For Information Only | Sulphurous/egg smell | A faint sulphurous smell | A faint sulphurous smell | A faint sulphurous smell | A sulphurous disappeared after 15 minutes |

| Test | Acceptance criteria | Comments (Batch D) | | | |
|---|---|---|---|---|---|
| | | Initial | 5° C. (24 months) | 25° C. (24 months) | 30° C. (24 months) |
| Appearance of Solution | Clear solution free from particulates | Complies | Complies | Complies | Complies |
| pH | >3.5 | 4.04 | 3.9 | 3.85 | 3.85 |
| CBD Content (%) | Within ±3% of initial | 100.0 | 97.6 | 95.8 | 95.9 |
| Degradants (% of CBD content) | | | | | |
| CBE I | NMT 1.0% | 0.00 | 0.00 | 0.00 | 0.00 |
| OH-CBD | NMT 1.0% | 0.05 | 0.00 | 0.01 | 0.34 |
| Individual unspecified degradants | Monitor Above 0.1% | RRT 1.90: 0.08 | RRT 1.90: 0.08 | RRT 1.90: 0.09 | RRT 1.90: 0.11 |
| Odour | For Information Only | Sulphurous/egg smell | A faint sulphurous smell | A sulphurous smell | A faint sulphurous smell |

TABLE 15

| Test | Acceptance criteria | Comments (Batch E) | | | | |
|---|---|---|---|---|---|---|
| | | Initial | 5° C. (12 months) | 25° C. (12 months) | 30° C. (12 months) | 40° C. (12 months) |
| Appearance of Solution | Clear solution free from particulates | Complies | Cloudy colourless liquid | Complies | Complies | Cloudy colourless liquid |
| pH | >3.5 | 4.10 | 3.96 | 3.86 | 3.98 | 4.05 |
| CBD Content (%) | Within ±3% of initial | N/D | N/A | N/A | N/A | N/A |
| Degradants (% of CBD content) | | | | | | |
| CBE I | NMT 1.0% | N/D | N/A | N/A | N/A | N/A |
| OH-CBD | NMT 1.0% | N/D | N/A | N/A | N/A | N/A |
| Individual unspecified degradants | Monitor Above 0.1% | N/D | N/A | N/A | N/A | N/A |
| Odour | For Information Only | Sulphurous/egg smell | A faint sulphurous smell | A faint sulphurous smell | A sulphurous smell | A sulphurous smell >30° C. |

| Test | Acceptance criteria | Comments (Batch E) | | | |
|---|---|---|---|---|---|
| | | Initial | 5° C. (24 months) | 25° C. (24 months) | 30° C. (24 months) |
| Appearance of Solution | Clear solution free from particulates | Complies | Complies | Complies | Complies |
| pH | >3.5 | 4.04 | 4.11 | 4.02 | 4.01 |
| CBD Content (%) | Within ±3% of initial | N/D | N/D | N/D | N/D |
| Degradants (% of CBD content) | | | | | |
| CBE I | NMT 1.0% | N/D | N/D | N/D | N/D |
| OH-CBD | NMT 1.0% | N/D | N/D | N/D | N/D |
| Individual unspecified degradants | Monitor Above 0.1% | N/D | N/D | N/D | N/D |
| Odour | For Information Only | Sulphurous/egg smell | A sulphurous smell | A sulphurous smell | A sulphurous smell |

TABLE 16

| Test | Acceptance criteria | Batch F (CBDV) | | | | |
| --- | --- | --- | --- | --- | --- | --- |
| | | Initial | 5° C. (12 months) | 25° C. (12 months) | 30° C. (12 months) | 40° C. (12 months) |
| Appearance of Solution | Clear solution free from particulates | Complies | Complies | Complies | Complies | Complies |
| pH | >3.5 | 4.15 | 3.99 | 4.06 | 4.04 | 4.06 |
| CBDV Content (%) | Within ±5% of initial | 100.0 | 100.4 | 100.9 | 99.9 | 99.5 |
| CBD | | 3.1 | 3.1 | 3.1 | 3.1 | 3.1 |
| CBD-4 | | 0.1 | 0.1 | 0.1 | 0.1 | 0.1 |
| Degradants (% of CBDV content) | | | | | | |
| CBE I | NMT 0.5% | <0.5 | <0.5 | <0.5 | <0.5 | <0.5 |
| OH-CBD | NMT 0.5% | <0.5 | <0.5 | <0.5 | <0.5 | <0.5 |

Conclusions

Batches A and F provides a shelf life based on the decision tree for evaluation of stability data (ICH guidelines) extended to 24 months.

Batch E is the corresponding placebo to Batch A and supports a store below 25° C. label.

As this product is intended for use in Climatic Zones I and II the intermediate condition will be used for assigning the shelf life based on the ICH decision tree.

Data for this formulation can support for an active formulation:

Climatic Zone I and II-24 months—Store below 25° C.

Climatic Zone III and IV-12 month—Store below 30° C.

In addition to the Stability study the formulation underwent a number of additional studies the results of which are set out below:

Experiment 2

Filtration Compatibility Study

A pre and post filtration study was carried out on the active and Placebo formulations.

The IV solution undergoes a bioburden reduction step after manufacture of the solution prior to filling using a Merck Millipore gold pack PVDF 0.22 μm filter. To determine compatibility of this filter a pre and post filtration sample was collected for both active and placebo batches. Assay, appearance, odour and pH was tested and the data is presented in Table 17.

TABLE 17

| Test Description | Pre filtration Active | Post filtration Active | Pre filtration Placebo | Post filtration Placebo |
| --- | --- | --- | --- | --- |
| Appearance | Clear colourless solution free from particulates | Clear colourless solution free from particulates | Clear colourless solution free from particulates | Clear colourless solution free from particulates |
| pH | 4.05 | 4.01 | 4.08 | 4.12 |
| Assay (CBD content) | 3.0 mg/mL | 3.0 mg/mL | ND | ND |
| Degradants | No change | No change | No change | No change |
| Odour | Faint egg like odour | Faint egg like odour | Faint egg like odour | Faint egg like odour |

Results from the pre and post filtration study demonstrates that the CBD IV solution and placebo are compatible with the tubing and filter used.

Experiment 3

Pilot Photostability Testing

A sample of placebo and active was prepared and packaged in 20 mL clear glass vials containing the IV solution. Two vials of active and two vials of placebo were subjected to a minimum of 1.2 million Lux hours as part of ICH Q1B testing. Additional vials were wrapped in foil as the control for the study.

Results

The experiment demonstrated no differences in appearance, pH, assay, degradants and odour between the control and test samples when exposed to 1.2 million Lux hours and the data is presented in Table 18.

TABLE 18

| Test Description | Control | Active | Control Placebo | Placebo |
| --- | --- | --- | --- | --- |
| Appearance | Clear solution free from particulates | Clear solution free from particulates | Clear solution free from particulates | Clear solution free from particulates |
| pH | 3.91 | 3.89 | 3.86 | 3.86 |
| Assay (CBD content) | 3.0 mg/mL | 3.0 mg/mL | ND | ND |
| Degradants | No change | No change | No change | No change |
| Odour | Faint egg like odour | Faint egg like odour slightly stronger than control | Faint egg like odour | Faint egg like odour slightly stronger than control |

The solution throughout the study remained clear and free from particulates with a pH for both active and placebo of 3.9 with and without foil. The assay results show no significant differences between the exposed vial and the control vial wrapped in foil.

Conclusion:

The product is not sensitive to light and a clear glass vial is suitable for storage and presentation of the CBD IV and Placebo solution.

Experiment 4

Compatibility in 5% Glucose Diluent

The proposed method of delivery for e.g. an IV product for neonatal hypoxia is slow bolus injection (Potentially via a catheter).

To test compatibility with a diluent, 30 mL of a 3 mg/mL CBD solution (90 mg) was injected into a 500 mL 5% glucose infusion bag and left for a period of 24 hours at ambient to determine any physical or chemical incompatibility.

5 mL samples were removed from the infusion bag using a 5 mL syringe on the outlet valve at 0, 0.5, 1, 2, 4 and 24 hours after injection. At each time point the bag was inspected under a polarised light box to check for any precipitation. The results are illustrated in Table 19 below.

TABLE 19

|  | 0 | 0.5 | 1 | 2 | 4 | 24 |
|---|---|---|---|---|---|---|
| CBD (calculated mg/mL) | 0.163 | 0.163 | 0.164 | 0.164 | 0.164 | 0.164 |
| Appearance (Clear solution free from particulates) | Complies | Complies | Complies | Complies | Complies | Complies |

At all time points the solution remained clear and free from particulates. There was some residual volume in the syringe and the needle that may account for the mass balance. CBD IV solution is compatible with glucose 5% for a period of 24 hours tested.

Conclusion:

The rationale for the 5% glucose infusion bag stems from the properties being very similar to the IV formulation with a pH of approximately 4 and an osmolality of close to 300 (maintaining isotonicity).

CBD IV solution is compatible with glucose 5% for a period of 24 hours tested. In addition, the pH remains unchanged over the 24 hour period and maintains pH of the glucose infusion bag of approx. 4.2.

Experiment 5

Particle Size

The preferred formulation was tested on a Malvern Zetasizer in order to measure the particle size of the micelles produced by the formulation.

Table 20 below details the average size of the particles of four batches of the formulation. As can be seen the particle size of all formulations is very consistent. All batches were shown to produce average micelle size of less than 20 nanometers. Such particle size may be important to enable faster uptake of the active agent into cells.

TABLE 20

| Sample Details | Date of Manufacture | Date of Testing | Z-Average (d · nm) |
|---|---|---|---|
| 3 mg/mL CBD IV | 15 Dec. 2015 | 11 May 2017 | 15.03 |
| 3 mg/mL CBD IV DSP-14-09-01 25° C. | 22 Sep. 2014 | 05 May 2017 | 17.02 |
| 3 mg/mL CBD IV DSP-15-06-01 25° C. | 15 Apr. 2015 | 19 Apr. 2017 | 15.45 |
| 3 mg/mL CBD IV | 03 Jun. 2015 | 03 May 2017 | 15.37 |

The invention claimed is:

1. An aqueous parenteral formulation comprising:
   (i) about 0.3 mg/mL to about 50 mg/mL of a cannabinoid comprising cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV), tetrahydrocannabivarinic acid (THCVA), or combinations thereof;
   (ii) about 5 mg/mL to about 50 mg/mL of an isotonic agent comprising glucose, polyethylene glycol, or glycerol;
   (iii) about 5 mg/mL to about 500 mg/mL of a non-ionic surfactant comprising polyoxyethylene (20) sorbitan monooleate, macrogol 15 hydroxystearate, or polyoxamers; and
   (iv) about 0.1 mg/mL to about 10 mg/mL of one or more stability enhancers comprising ascorbic acid, monothioglycerol, cysteine HCl, glutathione, disodium EDTA, calcium disodium EDTA, or combinations thereof;
   wherein the formulation has an osmolality of from 100-500 mOsMol/Kg; and
   wherein the formulation has a shelf-life of at least about 12 months.

2. The formulation of claim 1, wherein the cannabinoid is CBD or CBDV.

3. The formulation of claim 1, wherein the isotonic agent is glycerol or glucose.

4. The formulation of claim 1, wherein the isotonic agent is glycerol.

5. The formulation of claim 1, wherein the non-ionic surfactant is polyoxyethylene (20) sorbitan monooleate or macrogol 15 hydroxystearate.

6. The formulation of claim 1, wherein the non-ionic surfactant is macrogol 15 hydroxystearate.

7. The formulation of claim 1, wherein the one or more stability enhancers is ascorbic acid, monothioglycerol, or a combination thereof.

8. The formulation of claim 7, wherein when the ascorbic acid is present, the ascorbic acid is present in an amount of from 0.5 to 10 mg/ml, or when monothioglycerol is present, the monothioglycerol is present in an amount of from 0.5 to 10 mg/ml.

9. The formulation of claim 1, having a pH ranging from about 3.5 to about 4.13.

10. The formulation of claim 1, having a pH of about 4.

11. The formulation of claim 1, wherein the non-ionic surfactant is macrogol 15 hydroxystearate, the isotonic agent is glycerol, and the stability enhancer is ascorbic acid, monothioglycerol, calcium disodium EDTA, disodium EDTA, or combinations thereof.

12. The formulation of claim 1, having a shelf life of at least about 18 months.

13. The formulation of claim 1, having a shelf life of at least about 24 months.

14. The formulation of claim 1, wherein the formulation is stable in climatic zones 1 and 2 for about 12-24 months.

15. The formulation of claim 1, wherein the formulation is stable in climatic zones 3 and 4 for about 12-24 months.

16. The formulation of claim 1, wherein the cannabinoid content remains within ±3% of the initial content when tested over 12 months at temperatures ranging from 5-40° C.

* * * * *